US009952219B2

(12) United States Patent
Pond et al.

(10) Patent No.: US 9,952,219 B2
(45) Date of Patent: Apr. 24, 2018

(54) COMPOSITIONS AND METHODS FOR DETECTING ORAL NEOPLASM

(71) Applicant: Inter-Med, Inc., Racine, WI (US)

(72) Inventors: Gary Pond, Milwaukee, WI (US); John Baeten, Oak Creek, WI (US)

(73) Assignee: Inter-Med, Inc., Racine, WI (US)

( * ) Notice: Subject to any disclaimer, the term of this patent is extended or adjusted under 35 U.S.C. 154(b) by 0 days.

(21) Appl. No.: 14/869,316

(22) Filed: Sep. 29, 2015

(65) Prior Publication Data
US 2016/0018398 A1 Jan. 21, 2016

Related U.S. Application Data

(63) Continuation of application No. 12/715,159, filed on Mar. 1, 2010, now abandoned.

(60) Provisional application No. 61/208,730, filed on Feb. 27, 2009.

(51) Int. Cl.
*G01N 33/574* (2006.01)
*A61B 5/00* (2006.01)
*A61B 19/02* (2006.01)
*A61K 49/00* (2006.01)
*A61B 50/33* (2016.01)

(52) U.S. Cl.
CPC ..... *G01N 33/57407* (2013.01); *A61B 5/0071* (2013.01); *A61B 5/0088* (2013.01); *A61B 50/33* (2016.02); *A61K 49/0056* (2013.01); *A61B 2562/0233* (2013.01); *G01N 2333/42* (2013.01)

(58) Field of Classification Search
None
See application file for complete search history.

(56) References Cited

U.S. PATENT DOCUMENTS 7,776,550 B2 * 8/2010 Block ............. G01N 33/57438
435/7.1
2009/0220415 A1 * 9/2009 Shachaf ............. A61B 5/0071
424/1.11

OTHER PUBLICATIONS

Mazumdar et al., Int J Oral Maxillofac Surg., 1993, 22(5): 301-305.*
Prime et al., J. Pathol., 1985, 147:173-179.*
Carlson et al., Technol Cancer Res Treat, Oct. 2007, 6(5):361-374.*
Sakuma et al., Journal of Controlled Release, 2009, 134:2-10, available online: Oct. 31, 2008.*
Ridley et al., IADR Abstracts, 1992, 706.*

* cited by examiner

*Primary Examiner* — Hong Sang
(74) *Attorney, Agent, or Firm* — Boyle Fredrickson S.C.

(57) ABSTRACT

Methods and kits for assessing the presence of, and for detecting cancer, notably oral cancer, are disclosed. Such methods and kits use one or more lectins operably linked to a fluorophore, wherein the lectin binds differentially to cancerous and non-cancerous tissues, and wherein the fluorophore facilitates visualizing the differential binding. The lectins are applied to the oral mucosa of a subject, the fluorophore is exposed to light, and cancerous regions of the mucosa are visualized. In certain embodiments, the lectin specifically binds to one or more of a β-galactoside, an α- or β-N-acetylglucosamine, or a sialic acid moiety.

14 Claims, 29 Drawing Sheets

COMPOSITIONS AND METHODS FOR DETECTING ORAL NEOPLASM

CROSS-REFERENCE TO RELATED APPLICATIONS

This application is a continuation of U.S. application Ser. No. 12/715,159 filed on Mar. 1, 2010 (now abandoned), which claims the benefit of U.S. Provisional Application No. 61/208,730 filed on Feb. 27, 2009. Each of these applications is incorporated herein by reference as if set forth in its entirety.

STATEMENT REGARDING FEDERALLY SPONSORED RESEARCH OR DEVELOPMENT

N/A

BACKGROUND

The present invention relates to methods, devices and kits for use in screening patients to detect cancers and precancers associated with mucosal tissues, particularly oral cancer, using optical molecular imaging.

Cancer is defined as the uncontrollable growth of cells that invade and cause damage to surrounding tissue. Many properties of mammalian cells are either expressed at or mediated through the cell surface, and cancer is associated with characteristic molecular changes on the cellular surface.

Specifically, membrane proteins and lipids having attached carbohydrate side chains project from the external surface of a cell and form the cell glycocalyx. The glycosyl structures of these carbohydrate side chains vary among different cell types, among the same cells in different stages of the maturation process, and during pathological changes such as cancer (see, e.g., Ramsey I S, Delling M and Clapham D E, Annu Rev Physiol 2006; 68: 619-47; Gunthorpe M J and Chizh B A, Drug Discov Today 2009; 14: 56-67; Pankratov Y V, Lalo U V and Krishtal O A, J Neurosci 2002; 22: 8363-9). The side chains are heterogeneous in their oligosaccharide composition, length and branching status, conferring distinct biochemical and antigenic properties of the glycoconjugates, as, for example, with the idiotypic blood group antigens present on epithelial cells. These side chains also play an important role in regulating cell proliferation (see Feske S et al., Nature 2006; 441: 179-85; Cahalan M D, Nat Cell Biol 2009; 11: 669-77). Altered glycosylation of cell surface proteins, especially the terminal glycoprotein epitopes, may play a significant role in cell-cell interactions, development of cell adhesion, malignant transformation, and metastasis.

Altered glycosylation is a universal feature of cancer cells, and certain types of glycan structures are well-known markers for tumor progression (Varki A, Cummings, E. et al Editors, Essentials of Glycobiology, Cold Spring Harbor Laboratory Press Cold Spring Harbor, New York). Aberrant glycosylation occurs in essentially all types of experimental and human cancers, as has been observed for over 35 years, and many glycosyl epitopes constitute tumor-associated antigens. A long-standing debate is whether aberrant glycosylation is a result or a cause of cancer. Many recent studies indicate that some, if not all, aberrant glycosylation is a result of initial oncogenic transformation, as well as a key event in induction of invasion and metastasis.

Glycosylation promoting or inhibiting tumor cell invasion and metastasis is of crucial importance in current cancer research. Nevertheless, this area of study has received little attention from most cell biologists involved in cancer research, mainly because structural and functional concepts of glycosylation in cancer are more difficult to understand than the functional role of certain proteins and their genes in defining cancer cell phenotypes. Glycosylation appears to be considered "in the shade" of more popular topics such as oncogenes and antioncogenes, apoptosis, angiogenesis, growth factor receptors, integrins and adherins function, etc., despite the fact that aberrant glycosylation profoundly affects all of these processes (Senitiroh Hakomori, Glycosylation defining cancer malignancy: New wine in an old bottle. PNAS, Aug. 6, 2002, vol. 99, no. 16 10231-10233).

The carbohydrate side chains discussed above form receptor sites for lectins, which are non-enzymatic proteins or glycoproteins of non-immune origin that bind specifically and non-covalently to specific oligosaccharide chains (see Brandman O et al., Cell 2007; 131: 1327-39). Lectins can thus serve to identify cell types or cellular components and have become useful analytical tools for studying the altering of cell surface carbohydrates in disease stages (Roderick H L and Cook S J, Nat Rev Cancer 2008; 8: 361-75). During post-translational events and in the course of disease, including cancer, cellular proteins are modified, often by changing the glycosylation of the cellular proteins. Thus, lectins can be used as targets for identifying cell surface changes associated with cancers and other conditions.

Some lectins recognize oligosaccharides only, while others bind both oligosaccharides and monosaccharides (mannose, galactose/N-acetyl galactosamine, N-acetyl glucosamine, fucose, and sialic acid). Monosaccharide-specific lectins are usually classified according to one of five groups depending upon its highest-affinity monosaccharide.

Even so, most lectins interact with more than one group, albeit at a lower association constant, such that it can be difficult to associate binding of a particular lectin with a specific disease. Some lectins can interact with monosaccharides from different specificity groups through the same binding site. Other lectins can bind simultaneously with distinct sugars. Still others can combine with monosaccharides that appear structurally unrelated, but that present similar topographical features when appropriately viewed.

For example, WGA binds N-acetyl glucosamine and, more weakly, N-acetyl galactosamine. WGA also binds N-acetyl neuraminic acid in free form because this monosaccharide is structural similar to N-acetyl glucosamine. Many monosaccharide-specific lectins can be classified according to the type of protein-linked carbohydrate unit they recognize. As such, some lectins react primarily with O-linked sugar units, whereas others bind N-linked units.

Although each unique lectin has a higher specificity for certain groups, very few lectins bind only a single sugar unit and each lectin provides distinctly different background binding properties and signal-to-noise ratios in tissue.

Lectins are found in plants, animals, and fungi, and a variety of lectins are known in the art. The carbohydrate binding specificity of a number of commercially available lectins is well known in the art (see e.g. Lectin and Lectin Conjugates Catalog Addendum, EY Laboratories, Inc., San Mateo, Calif., 2010). A non-limiting list of commercially available plant lectins is shown by organism of origin and standard abbreviation in Table 1 below. In addition, new lectins are discovered each year.

TABLE 1

Selected Commercially Available Lectins (adapted from Lectin and Lectin Conjugates Catalog Addendum, EY Laboratories, Inc., San Mateo, California, 2010).

| Lectin source (Latin name) | Common name | Abbreviation |
| --- | --- | --- |
| *Abrus precatorius* | jequirity bean | APA |
| *Aegopodium podagraria* | ground elder | APP |
| *Agaricus bisporus* | mushroom | ABA |
| *Allomyrina dichotoma* | Japanese beetle | Allo A |
| *Anguilla Anguilla* | fresh water eel | AAA |
| *Arachis hypogaea* | peanut | PNA |
| *Artocarpus integrifolia* | jackfruit | Jacalin AIA |
| *Bauhinia purpurea* | camel's foot tree | BPA |
| *Bryonia dioica* | white bryony | BDA |
| *Canavalia ensiformis* | jack bean | Con A |
| *Cancer antennarius* | California crab | CCA |
| *Caragana arborescens* | pea tree | CAA |
| *Cicer arietinum* | chick pea, ceci bean | CPA |
| *Colchicum autumnale* | meadow saffron | CA |
| *Cytisus scoparius* | scotch broom | CSA |
| *Datura stramonium* | jimson weed | DSA |
| *Dolichos biflorus* | horse gram | DBA |
| *Erythrina cristagalli* | coral tree | ECA |
| *Euonymus europaeus* | spindle tree | EEA |
| *Galanthus nivalis* | snowdrop | GNA |
| *Glycine max* | soybean | SBA |
| *Griffonia simplicifolia* | | GS-I, GS-II |
| *Helix aspersa* | garden snail | HAA |
| *Helix pomatia* | edible snail | HPA |
| *Homarus americanus* | California lobster | HMA |
| *Iberis amara* | | IAA |
| *Laburnum alpinum* | scotch alburnum | LAA |
| *Lens culinaris* | lentil | LcH |
| *Limax flavus* | garden slug | LFA |
| *Limulus polyphemus* | horseshoe crab | LPA |
| *Lotus tetragonolobus* | asparagus pea | Lotus |
| *Lycopersicon esculentum* | tomato | LEA |
| *Maackia amurensis* | *maackia* | MAA |
| *Maclura pomifera* | osage orange | MPA |
| *Mangifera indica* | mango | MIA |
| *Narcissus pseudonarcissus* | daffodil | NPA |
| *Perseau americana* | avocado | PAA |
| *Phaseolus lunatus* | lima bean | LBA |
| *Phaseolus vulgaris* | red kidney bean | PHA-L, PHA-E PHA-P, PHA-M |
| *Phaseolus vulgaris* | black kidney bean black bean | |
| *Phytolacca americana* | pokeweed | PWM, PWA |
| *Pisum sativum* | garden pea | PSA, PEA |
| *Psophocarpus tetragonolobus* | winged bean | PTA |
| *Ricinus communis* | castor bean | RCA-I, RCA-II |
| *Robinia pseudoacacia* | black locust | RPA |
| *Salvia horminum* | *salvia* | SHA |
| *Salvia sclarea* | *salvia* | SSA |
| *Sambucus nigra* | elderberry | SNA |
| *Solanum tuberosum* | potato | STA |
| *Sophora japonica* | Japanese pagoda tree | SJA |
| *Trichosanthes kirilowii* | tianhuafen, China gourd | TKA |
| *Trifolium repens* | white clover | RTA |
| *Triticum vulgare* | wheat germ | WGA |
| *Tulipa* sp | tulip | TL |
| *Ulex europaeus* | gorse or furze | UEA-I, UEA-II |
| *Urtica dioica* | stinging nettle | UDA |
| *Vicia faba* | fava bean, broad bean | VFA |
| *Vicia graminea* | | VGA |
| *Vicia villosa* | hairy vetch | VVA |
| *Vigna radiate* | mung bean | VRA |
| *Viscum album* | mistletoe | VAA |
| *Wisteria floribunda* | Japanese *wisteria* | WFA |

Possible Lectin Targets.

A number of cell surface carbohydrate moieties are known to undergo both qualitative and quantitative change as cells are pathologically transformed, including in precancers or cancers. Such moieties are potential targets for lectin-based methods of detecting pathological transformation. The following is a non-limiting review of some of the carbohydrate moieties that are known to undergo such changes.

Cell Surface/Blood Group Antigens.

Malignant transformation that results in disordered cell surface carbohydrate expression is often associated with glycosylation changes in the carbohydrates that can include (1) synthesis of new carbohydrate structures and (2) deletion of more complex structures and accumulation of smaller precursor structures. Although originally described as major erythrocyte antigens, blood group antigens are found on epithelial cells of various tissues including oral mucosa.

In mucosal squamous cell carcinoma in the head and neck, especially in oral cancer, incomplete glycosylation of cell surface carbohydrates of the ABO(H) blood group antigens is significant (Dabelsteen et al., Acta Pathol Microbiol Scand. 1988: 17: 506-511; Mandel et al., J Oral Pathol. 1988; 17: 506-511). A-, B-, and H blood group antigens carry their specific antigenic determinants at the ends of their carbohydrate chains. The A or B-antigens and their immediate precursor, H-antigen, are carried by branched or unbranched type 1 ([Galβ1→3GlcNAc]$_n$β1→3Gal→R) or type 2 ([Galβ1→4GlcNAc]$_n$β1→3Gal→R) chains, in which Gal is D-galactose and GlcNAc is N-acetyl-D-glucosamine, depending on the type of tissues (e.g. in gastrointestinal epithelia and their secretions, antigens are carried predominantly by type 1 chains, while in erythrocytes they are carried by type 2 chains) (Feske S et al, Nature 2006; 441: 179-85; Endo Y et al, Int J Cancer 2004; 110: 225-31). A and B antigens expressed in normal epithelial cells are lost or diminished, while the precursor H antigen is strongly expressed in the same malignant cells.

In addition, cell surface expression Lewis determinants displayed on the terminus of glycolipids are modified during carcinogenesis and metastasis. The Lewis determinants are structurally related to determinants of the ABO and the H/h blood group systems. They are assembled by sequential addition of specific monosaccharides onto terminal saccharide precursor chains on glycolipids or glycoproteins. The ABH and Lewis glycoproteins possess a common basic structure and their blood group specificity is determined by the sequence and linkage. There are two Lewis antigens, termed Le-a and Le-b. The presence of fucose linked to C-4 of N-acetylglucosamine on a Type 1 chain results in Le-a activity, but a Type 2 oligosaccharide containing fucose linked to C-3 of N-acetylglucosamine on a Type 2 chain results in very weak Le-a activity. The appearance of a second fucose on a type one chain results in the appearance of a new antigenic determinant, Le-b, and the loss of most H and Le-a antigenicity. A Type 2 difucosyl chain has very weak Le-b activity. Since these blood group antigens are associated with carbohydrate side chains of cell surface glycoconjugates, lectins or antibodies could be used to highlight aberrant glycosylation associated with cancerous lesions.

Thomsen-Friedenreich Antigen(s).

The Thomsen-Friedenreich (TF) antigen, a well-defined pan-carcinoma antigen associated with a variety of cancers in different tissues (Monteith G R and Roufogalis B D, Cell Calcium 1995; 18: 459-70), has been targeted recently for the development of tumor selective vaccines (Putney J W Jr, Nat Cell Biol 2009; 11: 381-382). During carcinogenesis, T, Tn and sialyl Tn antigens, core O-linked glycoprotein structures, are formed when core carbohydrate structures are incompletely glycosylated (Saussez S et al., Cancer, 1998; 15:252-260). In oral cancers, the Thomsen-Friedenreich antigen is abundantly expressed in well-differentiated squamous cell carcinomas, and therefore these glycol structures offer possible binding sites for lectins and anti-TF antigen antibodies.

Mucins and Mucin-Like Proteins.

Mucins are large glycoproteins with a "rod-like" conformation caused by the presence of many clustered glycosylated serines and threonines in tandem repeat regions. Most epithelial mucin polypeptides belong to the MUC family. In the normal polarized epithelium, mucins are expressed exclusively on the apical domain, toward the lumen of the organ. Likewise, soluble mucins are secreted exclusively into the lumen. However, the loss of correct topology in malignant epithelial cells allows mucins to be expressed on all aspects of the cells, and soluble mucins can then enter the extracellular space and body fluids such as the blood plasma. In many instances, mucins appear to be the major carriers of altered glycosylation in carcinomas. Another abnormal feature of carcinoma mucins is incomplete glycosylation. Glandular epithelial tissues synthesize and secrete high molecular weight mucin and mucin-like glycoproteins containing O-linked oligosaccharide chains (chains which are branched off of serine or threonine). Under certain pathological conditions, including malignant transformation, the rate of production and degree of glycosylation of these glycoproteins is altered, frequently as a result of incomplete assembly of the normal cell surface structures (Putney J W and Bird G S, J Physiol 2008; 586: 3055-9; Catterall W A et al. Pharmacol Rev 2005; 57: 411-25).

During carcinogenesis, human secretory mucin (MUC) genes can also be misregulated, thereby further affecting mucin levels. MUC1 (polymorphic epithelial mucin, Episialin, MAM-6 antigen, epithelial membrane antigen), a membrane-associated mucin expressed in many secretory epithelia, is expressed at a low level in normal oral mucosa (Gunthorpe M J and Chizh B A, Drug Discov Today 2009; 14: 56-67; Pankratov Y V, Lalo U V and Krishtal O A, J Neurosci 2002; 22: 8363-9). The other MUC genes include MUC2 (prominent in the small and large intestine), MUC3 (predominant in the small intestine), MUC4 (universal for the epithelia), MUC5B (essentially in glandular acini in the submaxillary gland), MUC5C (present in respiratory and gastric tracts) (Putney J W Jr, Nat Cell Biol 2009; 11: 381-3825; Putney J W and Bird G S, J Physiol 2008; 586: 3055-9), MUC6 (prominent in the stomach and gall bladder) (Catterall W A et al, Pharmacol Rev 2005; 57: 411-257) and MUC7 (mainly in the submandibullary gland) (Saponara S, Sgaragli G and Fusi F, Eur J Pharmacol 2008; 598: 75-80). Overexpression of the mucin proteins, especially MUC 1, is associated with many types of cancer.

Given the abundance of simple mucin-type O-glycosylation in oral and other mucosa (Putney J W Jr, Nat Cell Biol 2009; 11: 381-382), one or more novel membrane-associated mucin-like glycoproteins are likely modified by glycosylation and overexpressed during carcinogenesis, and these modifications can be targeted by lectins.

Fucosylation.

Fucosylation (the addition of L-fucose at an oligosaccharide chain terminus) mediates several specific biologic functions. Tumor cells escape recognition by increasing surface fucosylation levels, which leads to decreased adhesion and uncontrolled tumor growth. Monitoring serum/tissue fucose levels could be a promising approach for the early detection, diagnosis, and prognosis of various cancer types. As such, antibodies or lectins selective of L-fucose groups at the end of glycoconjugates could be used as a cancer detection scheme.

Sialylation or Desialylation.

Sialic acid's position at or near non-reducing termini underlies its vital role in determining surface characteristics of cells and secreted glycoproteins. Cell surface glycoconjugate oligosaccharides of cancer patients contain increased levels of the sialic acid, N-acetylneuraminic acid (Neu5Ac or NANA), the predominant sialic acid found in mammalian cells. Accordingly, glycoprotein-bound and glycolipid-bound sialic acid are important cancer biomarkers (Ramsey I S, Delling M and Clapham D E, Annu Rev Physiol 2006; 68: 619-47; Catterall W A et al, Pharmacol Rev 2005; 57: 411-25). Sialic acid content is typically measured either as total sialic acid (TSA; glycoprotein- and glycolipid-bound sialic acid) or as lipid-bound sialic acid (LSA; glycolipid-bound sialic acid) (Saponara S, Sgaragli G and Fusi F, Eur J Pharmacol 2008; 598: 75-80). Serum TSA and LSA levels are significantly elevated in sera of patients with oral and pharyngeal cancer compared with controls (Gunthorpe M J and Chizh B A, Drug Discov Today 2009; 14: 56-673). Additionally, elevated serum sialic acid levels are reported to be correlated with the clinical staging, prognosis and recurrence of malignancies (Pankratov Y V, Lalo U V and Krishtal O A, J Neurosci 2002; 22: 8363-9; Feske S et al, Nature 2006; 441: 179-85).

Although glycoprotein and glycolipid-bound sialic acid content and its correlation to diagnosis and detection of cancer has not been fully studied, lectins selective of sialic acid groups at the end of glycoconjugates may be useful for cancer detection.

Epidermal Growth Factor Receptor (EGFR).

EGFR, a 170 kDa transmembrane glycoprotein (member of the erbB family of cell surface receptors) that plays a role in several metabolic pathways, is composed of 3 major regions: an amino-terminal extracellular ligand-binding domain, a hydrophobic transmembrane domain and a cytoplasmic domain. The extracellular domain, more precisely the ligand-binding domain, is characterized by a relatively high content of carbohydrates that can be glycosylated.

EGFR overexpression is a well-established biomarker in premalignant and invasive oral squamous epithelial lesions. EGFR expression is detected at all stages of carcinogenesis, from normal-early hyperplasia, dysplasia to invasive carcinoma (Monteith G R et al, Nat Rev Cancer 2007; 7: 519-30; Jackson T R et al, Biochem J 1988; 253: 81-618, 19). EGFR expression is elevated during the progression from hyperplasia to dysplasia and increases during progression from dysplasia to invasive squamous cell carcinoma (SCC) (Pacifico F et al. J Mol Endocrinol 2003; 30: 399-40920). Interestingly, Nouri et al. (Int J Cancer 2004; 110: 225-3122) found that 73% of the invasive oral SCC they studied showed strong EGFR expression. Other reports have estimated overexpression of EGFR in all oral cancers at 50-98% (Prasad V et al. Cancer Res 2005; 65: 8655-6123).

Fluorescent dyes conjugated to monoclonal antibodies have been used to label EGFR on the surface of SiHa cervical cancer cells and in ex vivo human oral cavity biopsies (Ramsey I S, Delling M and Clapham D E. Annu Rev Physiol 2006; 68: 619-47). Gold nanoparticles and nanoshells (spherical nanoparticles having a core made of a dielectric material such as zinc selenide, sapphire, or glass, covered by a thin metallic shell) have also been used to target surface receptors in cell lines and ex vivo tissues. For example, nanoshells targeted with anti-Her2 have been used to label SK-BR-3 breast cancer cells in culture (Gunthorpe M J and Chizh B A, Drug Discov Today 2009; 14: 56-67), and gold nanoparticles conjugated to EGFR antibodies have been used to target EGFR on the surface of SiHa cervical cancer cells and in human cervical cancer biopsies (Pankratov Y V, Lalo U V and Krishtal O A. J Neurosci 2002; 22: 8363-9). Most recently, EGFR expression in oral neoplasia was investigated by conjugating an EGF peptide to Alexa-647 (a NIR fluorescent dye) and observing its binding ability on extracted oral cancers (Nitin, et al, Neoplasia 2009; 11:542-551).

In addition to changing EGFR expression, cancer also post-translationally modifies EGFR by phosphorylation, glycosylation, and by forming disulfide bridges. It is likely that all the carbohydrates on the EGFR (approximately 30 kDa) are present as N-linked oligosaccharide chains. Since EGFR is overexpressed in oral cancers, and the extracellular component of EGFR has a predictable post-glycosylation structure, lectins targeting this structure could effectively label EGFR to reveal oral cancer. Furthermore, VEGFR (vascular EGFR) is also overproduced in oral cancer, and could be a target of lectin-based detection. Nevertheless, to the best of our knowledge, EGFR labeling via lectins that specifically target EGFR or VEGFR has not been investigated as a means to detect cancerous tissue in-vitro, ex-vivo, or in-vivo.

In oral cancer, lesions appear as a growth or sore in the mouth that does not go away. Oral cancer, which includes cancers of the lips, tongue, cheeks, floor of the mouth, hard and soft palate, sinuses, and pharynx (throat), is life threatening if not diagnosed and treated early. The most common type of oral cancer is oral neoplasia or oral neoplasm, sometimes referred to as epithelial cancer, which is characterized as squamous cell carcinoma.

Out of the 400,000 individuals newly diagnosed each year with oral cancer, about half will die in the five years after diagnosis (Parekh A B and Putney J W Jr., Physiol Rev 2005; 85: 757-810). This number has not significantly improved over the past few decades, despite continued refinement of surgical techniques and screening technologies. The death rate for oral cancer is particularly high since it is not generally discovered until it has spread to other parts of the body. Because the early signs and symptoms may be misinterpreted by individuals and screening tests tend to be inconsistently employed, oral cancer may not be detected at early stages when it is most treatable. However, early detection and treatment of cancers can markedly decrease mortality rates and increase survival rates.

A patient's primary point of care for oral cancer detection is a general dental practitioner. As part of a routine dental exam, a dentist will conduct an oral cancer screening exam. More specifically, a dentist will feel for any lumps or irregular tissue changes in a patient's neck, head, face, and oral cavity. Recently, several commercially available technologies have been developed (i.e. ViziLite®, VELscope®, Trimira®, etc.) to screen for oral cancer. However, the effectiveness of these technologies to aid in the detection of oral cancers is inconsistent, and it appears these modalities fail to noticeably improve the detection of oral lesions from routinely preformed standard head and neck exams (Putney J W Jr., Nat Cell Biol 2009; 11: 381-382).

For those instances in which a patient has been diagnosed with cancer, the physician generally determines if the cancer can be removed or resected by surgery. Patients who have cancer that has not spread beyond a local area frequently may be treated by completely resecting the tumor. Prior to surgery, various images of the tumor are obtained such as X-rays, CT scans, MRI scans or PET images. Although such images provide guidance for surgery, these images cannot be generated in real time during surgery to guide the surgeon to the tumor.

What is needed are methods, devices and kits for detecting and identifying oral cancer tissue and potential surgical margins that are convenient, cost effective, and that can be used in a variety of clinical settings, including dental offices and operatories.

BRIEF SUMMARY

The invention provides methods, devices, and kits for detecting cancers and precancers associated with mucosal tissue, particularly cancer in the oral mucosa of a subject, using lectin-based probes targeting the molecular level cell surface changes associated with oral cancer.

In a first aspect, the invention encompasses a method for assessing the presence of possible oral cancer in a subject. The method includes the steps of (1) applying a composition comprising one or more lectins operably linked to a detection moiety to the oral mucosa of a subject, wherein said lectins specifically bind to one or more mono and/or oligosaccharides; (2) exposing the oral mucosa of the subject to near infrared light, visible light, or ultraviolet light; and (3) visualizing the oral mucosa to detect possible oral cancer.

In a second aspect, the invention encompasses a method for assessing the presence of possible oral cancer in a subject, including the steps of (1) applying one or more lectins to the oral mucosa of a subject, wherein said lectins specifically bind to one or more mono and/or oligosaccharides; (2) applying an antibody or an avidin protein to the oral mucosa of the subject, wherein the antibody or avidin protein is linked to a fluorophore; (3) exposing the oral mucosa of the subject to near infrared light, visible light, or ultraviolet light; and (4) visualizing the oral mucosa to detect possible oral cancer.

In a third aspect, the invention encompasses a kit for assessing the presence of oral cancer. Such a kit includes (1) one or more lectins operably linked to a fluorophore, wherein said lectins specifically bind to one or more mono and/or oligosaccharides; and (2) a light source emitting light in the ultraviolet, visible, or near infrared spectrum.

The described embodiments have many advantages, including permitting simplified and more cost-effective detection of oral cancer through routine screening. These and other features, aspects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings.

FIG. 15 shows the person's gums after the tissue from FIG. 14 being removed, with the gums being prepared to receive bandages, gauze, or the like.

Figure 1:
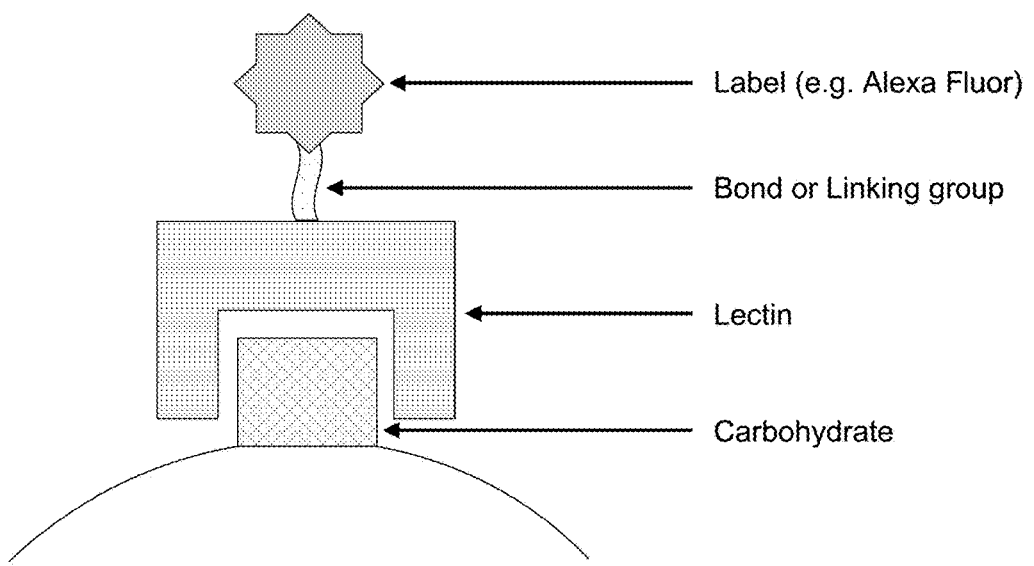
FIG. 1 is a schematic diagram showing a side view of a carbohydrate moiety on the surface of potentially cancerous oral mucosa tissue bound to a lectin linked to a "Label" to facilitate visualizing the location of the lectin.

While the present invention can be modified in various ways and includes many alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents and alternatives falling within the spirit and scope of the invention as defined by the appended claims.

DESCRIPTION OF PREFERRED EMBODIMENTS

The inventors report herein that certain specific classes of lectins differentially bind to cancerous mucosal tissue, notably oral mucosa. Such lectins can be operably linked to a detection moiety to obtain molecules or complexes that facilitate visualizing such differential binding. Accordingly, the invention includes lectin-based methods, devices and kits for detecting oral cancer in a subject.

In a first aspect, the invention encompasses a method for assessing the presence of oral cancer or precancer in a subject. The method includes the step of applying to the oral mucosa of a subject a composition comprising at least one lectin operably linked to a detection moiety. As used herein, the oral mucosa is the mucous membrane epithelium of the mouth. It includes (1) the masticatory mucosa, the keratinized stratified squamous epithelium found on the dorsum of the tongue, hard palate and attached gingiva; (2) the lining mucosa, the non-keratinized stratified squamous epithelium found almost everywhere else in the oral cavity; and (3) the specialized mucosa, the mucus membrane epithelium specifically in the regions of the taste buds on the dorsum of the tongue. Where oral cancer is present, the method is a method for detecting oral cancer. Since the method permits oral cancer to be visualized, the method steps can also be used in conjunction with a method for removing oral cancer.

When applied to the oral mucosa of the subject, the lectin(s) specifically bind to one or more targets associated with altered cell surface glycosylation in mucosal precancers and cancers, including oral cavity cancers, thus targeting and pinpointing the location of oral cancer by molecular targeting. The targeting lectins are operably linked to one or more detection moieties, facilitating detection of the binding location of the targeting lectins.

The inventors demonstrate herein that lectin-based molecular imaging can be used to detect oral cancers and precancers on human tissues from patients histologically confirmed to have oral cavity cancers or precancers, where the tissue samples had not been manipulated in any fashion (such as by using formaldehyde fixation or paraffin embedding). The lectin probes differentially bound to epithelial tissues sufficiently so that molecular imaging methods spatially resolved cancerous, precancerous, and normal tissue with a sufficiently high signal-to noise ratio to show that the method would be clinically useful. In particular, the inventors have demonstrated in the working examples below the successful use in the method of three different lectins, WGA, PNA, and GS-II, to detect oral cancer and precancer. To our knowledge, this is the first demonstration of lectin-based differential staining showing sufficient spatial contrast to detect oral cancers and precancers in a human patient.

Lectins bind generally to cell surface monosaccharide and oligosaccharide targets discussed previously. Thus, the method could be used with any known lectins that target such moieties. Table 2 below shows the specific carbohydrate moieties targeted by WGA, PNA, GS-II, and selected additional plant lectins. WGA is known to target both β-N-acetylglucosamine and sialic acid. PNA is known to target β-galactoside. GS-II is known to target both β-N-acetylglucosamine and α-N-acetylglucosamine.

TABLE 2

Targeted Moieties of Selected Plant Lectins (adapted from Lectin and Lectin Conjugates Catalog Addendum, EY Laboratories, Inc., San Mateo, California, 2010).

| Lectin Abbreviation | Known Targets |
| --- | --- |
| Con A | α-Man, α-Glc, α-GlcNAc |
| LcH | α-Man, α-Glc, α-GlcNAc |
| VFA | α-Man, α-Glc, α-GlcNAc |
| PSA | α-Man, α-Glc, α-GlcNAc |

TABLE 2-continued

Targeted Moieties of Selected Plant Lectins (adapted from Lectin and Lectin Conjugates Catalog Addendum, EY Laboratories, Inc., San Mateo, California, 2010).

| Lectin Abbreviation | Known Targets |
| --- | --- |
| GS-II | α-GlcNAc, β-GlcNAc |
| WGA | β-GlcNAc, Sialic Acid |
| DSA | β-GlcNAc |
| LEA | β-GlcNAc |
| STA | β-GlcNAc |
| LAA | β-GlcNAc |
| OSA | β-GlcNAc |
| PWM | β-GlcNAc |
| PWA | β-GlcNAc |
| UEA-II | β-GlcNAc |
| UDA | β-GlcNAc |
| PTA | β-Gal |
| HAA | α-GlcNAc, α-GalNAc |
| VAA | β-Gal |
| Allo A | β-Gal |
| ABA | β-Gal |
| APA | β-Gal |
| PNA | β-Gal |
| CSA | β-Gal |
| TKA | β-Gal |
| RCA-I | β-Gal |
| RCA-II | β-Gal |
| ECA | α-Gal, β-Gal, β-GalNAc, β-GalNAc |
| CAA | α-Gal, β-Gal, β-GalNAc, β-GalNAc |
| SNA | β-Gal, Sialic Acid |
| MAA | Sialic Acid |
| LFA | Sialic Acid |
| LPA | Sialic Acid |
| HMA | α-GalNAc, α-Fucose, Sialic Acid |
| CCA | Sialic Acid |

Accordingly, preferred lectin targets of the method include one or more of a β-galactoside, an α- or β-N-acetylglucosamine, or a sialic acid moiety. Preferably, the lectins used in the method would target one or more of these moieties, and such preferred lectins include Con A, LcH, VFA, PSA, GS-II, WGA, DSA, LEA, STA, LAA, OSA, PWM, PWA, UEA-II, UDA, PTA, HAA, VAA, Allo A, ABA, APA, PNA, CSA, TKA, RCA-I, RCA-II, ECA, CAA, SNA, MAA, LFA, LPA, HMA, and CCA. More preferably, the lectins used in the method would have the same target profile as WGA, PNA, or GS-II, and such more preferred lectins include GS-II, WGA, PNA, VAA, Allo A, ABA, APA, CSA, TKA, and RCA-I. Most preferably, the lectins used are one or more of GS-II, WGA, and PNA.

To facilitate detection of differential binding of the lectins to the oral mucosa of the subject, the lectins used in the invention are operably linked to a detection moiety. As used herein, "detection moiety" refers to a moiety that provides the ability to detect the location of the lectin. The detection moiety may be detected by such characteristics as color change, luminescence, fluorescence, reflectivity, or radioactivity. Examples of detection moieties known in the art include, but are not limited to, dyes, chemiluminescent compounds, enzymes, fluorescent compounds, metal complexes, biotin; haptens, radioluminescent compounds, radioactive-labeled biomolecules, colored microparticles, metallic nanoparticles, and quantum dots.

A preferred detection moiety used in the invention is a fluorophore. A fluorophore is a chemical species or moiety which causes a molecule to be fluorescent by absorbing energy of a specific wavelength and re-emitting energy at a different (but equally specific) wavelength. The difference between the absorption and emission wavelengths is known as a "Stokes shift." The intensity and wavelength of the emitted energy depend on both the fluorophore and the chemical environment within which the fluorophore exists.

A variety of fluorophores are known in the art, including fluorescent dyes, fluorescent nanoparticles, and proteins genetically engineered to fluoresce. Any known fluorophore could be used in the present invention. Non-limiting examples of fluorophores that could be used in the invention include fluorescein, fluorescein isothiocyanate (FITC), derivatives of rhodamine (such as TRITC), coumarin, cyanine, CF™ Dyes, any Fluo™ Probe, any DyLight® Fluor, any Oyster™ dyes, any Atto™ dye, any HiLyte Fluor™, and any Alexa® Fluor.

"Operably linked" as used herein broadly means that a direct or indirect attractive force exists between the lectin and the detection moiety of sufficient strength so that the lectin and the detection moiety are spatially associated. Although operably linked species may be covalently bonded or may be connected by the covalent bonding of both species to a common linker group, covalent bonding is not necessary for two species to be operably linked. Alternatively, operably linked species may be linked by intermolecular forces sufficient for the two species to remain spatially associated, such as hydrogen bonds and dipole-dipole interactions. In short, any binding between chemical species that is recognized in the art, such as antibody-antigen binding, target-receptor binding, enzyme-substrate binding, or biotin-avidin protein binding, is sufficient for two species to be operably linked.

"Binding" or "bound" as used herein broadly refer to any attractive interactions between two chemical species or moieties or the ongoing spatial association between chemical species or moieties caused by such attractive interactions. Although "binding" can refer to ionic or covalent bonds between two species, it also refers to attractive interactions facilitated by intermolecular forces such as hydrogen bonds, dipole-dipole interactions, or any other Van der Waals interaction between two species or moieties.

It is not necessary for operably linked species to be directly bound to each other or linked directly to each other. In certain embodiments of the invention, one or more chemical species may be interposed between the operably linked lectin and the detection moiety. If the interposed chemical species bind to each other, the lectin, and/or the detection moiety in such a way that the lectin and detection moiety are associated with the same complex of linked species, then the lectin and are operably linked.

In certain embodiments of the method, the lectin is directly bonded or linked to the detection moiety. FIG. 1 shows such an embodiment, where the lectin is bound to a cell surface carbohydrate. The lectin is shown linked to a fluorophore (designated the label, e.g. Alexa Fluor). In this embodiment, the lectin and the fluorophore may be linked by a covalent bond. Alternatively, the lectin and fluorophore may be both covalently bonded to a common linking group. As used herein, a "linking group" is a group of covalently bonded atoms that is itself covalently bonded to different two chemical species. The two chemical species are linked together through the covalent bonds to the common linking group.

Figure 2:
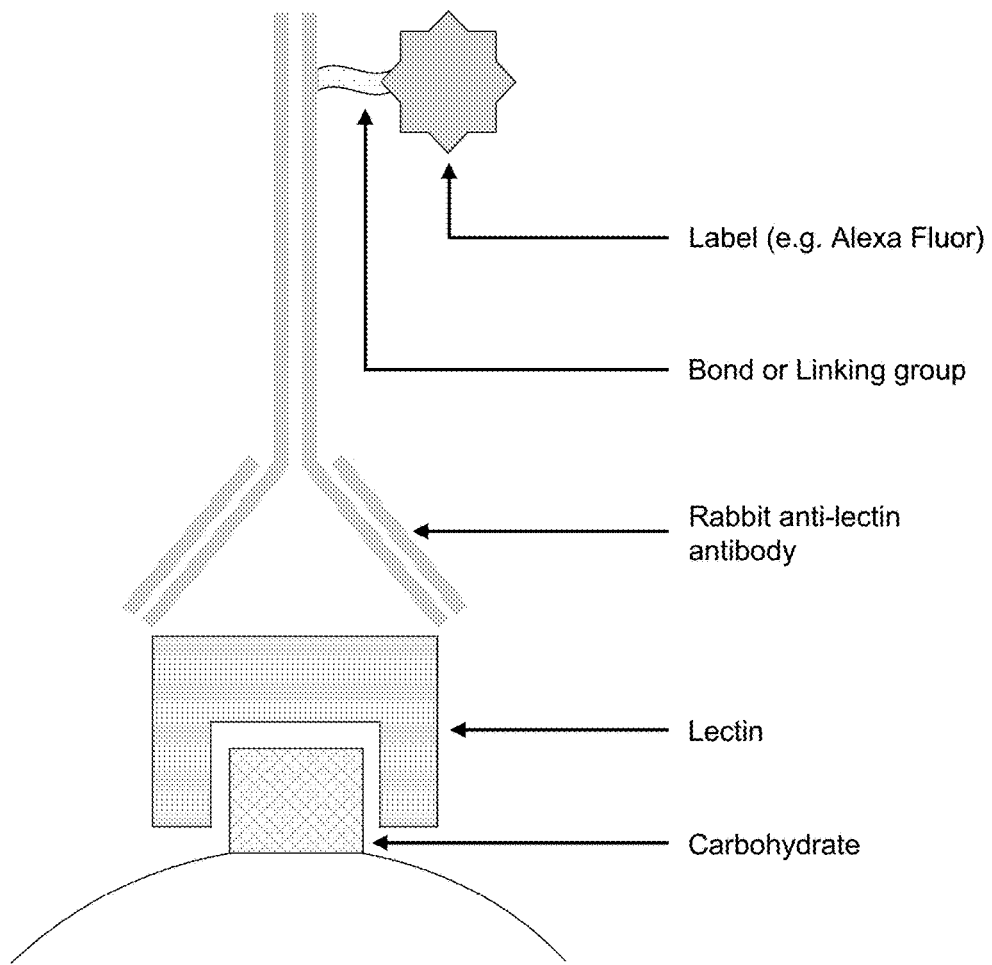
FIG. 2 is a schematic drawing showing a carbohydrate moiety on the surface of potentially cancerous oral mucosa tissue bound to a lectin. The Figure further shows an attractive interaction between the lectin and an anti-lectin antibody covalently linked to a "Label" to facilitate visualizing the location of the lectin.

In certain other embodiments, the lectin is linked indirectly to the detection moiety through one or more antibodies, one of which is covalently bonded to a detection moiety or linked to a detection moiety through a linking group covalently bonded to both the detection moiety and the antibody. FIG. 2 shows one such embodiment. As in FIG. 1, the lectin is bound to a cell surface carbohydrate. A rabbit anti-lectin antibody linked to a fluorophore (designated the label, e.g. Alexa Fluor) is bound to the lectin. Thus, the lectin is operably linked to the fluorophore.

Figure 3:
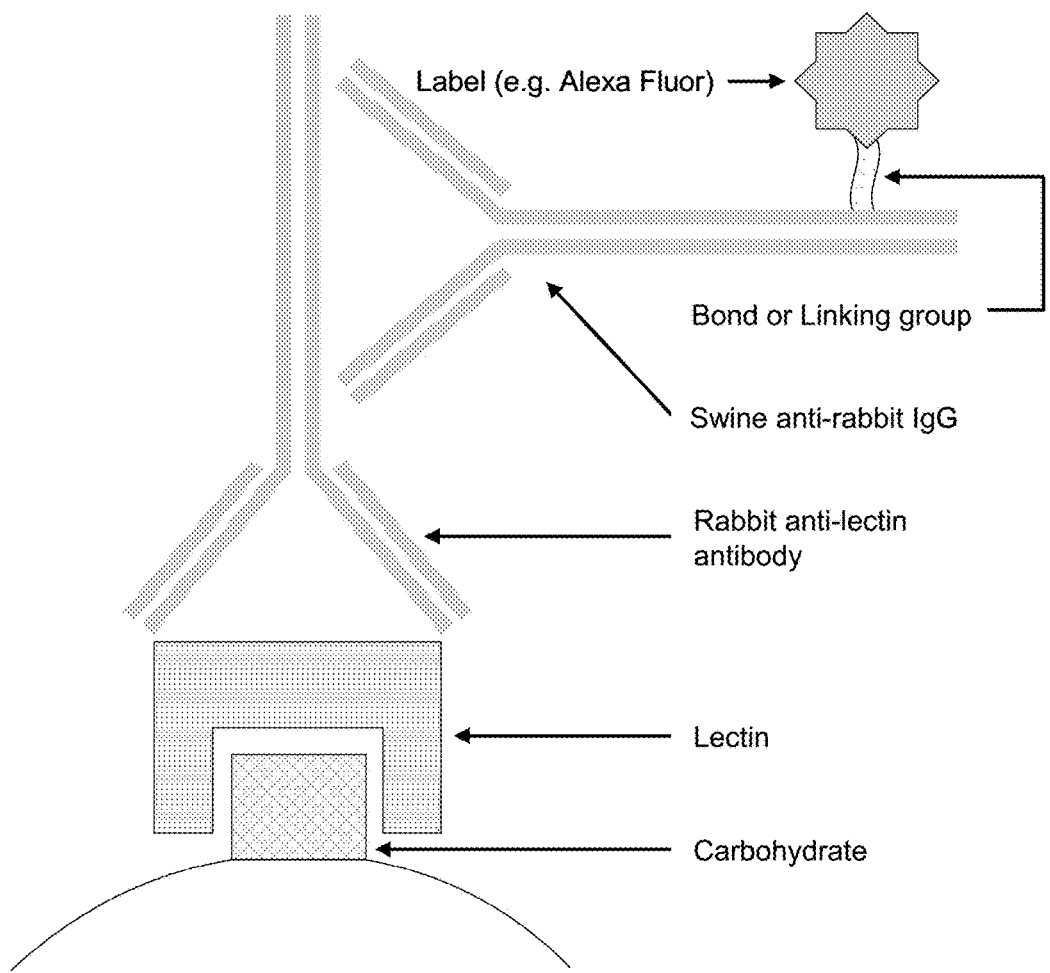
FIG. 3 is a schematic drawing showing a carbohydrate moiety on the surface of potentially cancerous oral mucosa tissue bound to a lectin. The Figure further shows an attractive interaction between the lectin and an anti-lectin antibody, and an attractive interaction between the anti-lectin antibody and a second antibody covalently linked to a "Label" to facilitate visualizing the location of the lectin.

FIG. 3 shows yet another such embodiment. In FIG. 3, the lectin is again shown bound to a cell surface carbohydrate. A rabbit anti-lectin antibody is bound to the lectin, and a second antibody (swine anti-rabbit IgG) linked to a fluorophore (designated the label, e.g. Alexa Fluor) is bound to the rabbit anti-lectin antibody. Once again, the lectin is operably linked to the fluorophore.

Figure 4:
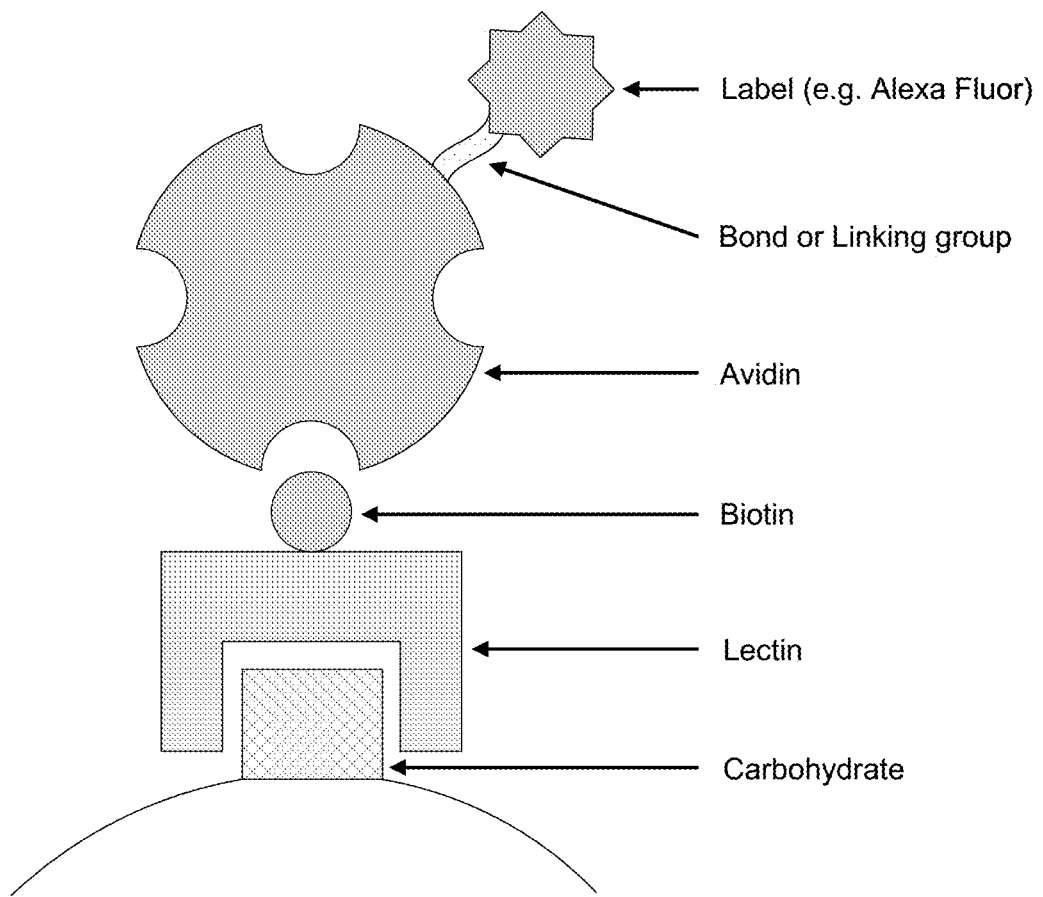
FIG. 4 is a schematic drawing showing a carbohydrate moiety on the surface of potentially cancerous oral mucosa tissue bound to a lectin linked to a biotin molecule. The Figure further shows an attractive interaction between the biotin and an avidin protein covalently linked to a "Label" to facilitate visualizing the location of the lectin.

In other embodiments, the lectin is linked indirectly to the detection moiety through a biotin molecule that is further bound to an avidin protein which is covalently bonded to a detection moiety or linked to a detection moiety through a linking group. FIG. 4 shows one such embodiment. The lectin is once again shown bound to a cell surface carbohydrate. A biotin molecule is bound to the lectin, and the biotin molecule binds to an avidin protein linked to a fluorophore (designated the label, e.g. Alexa Fluor). Thus, the lectin is operably linked to the fluorophore.

Figure 5:
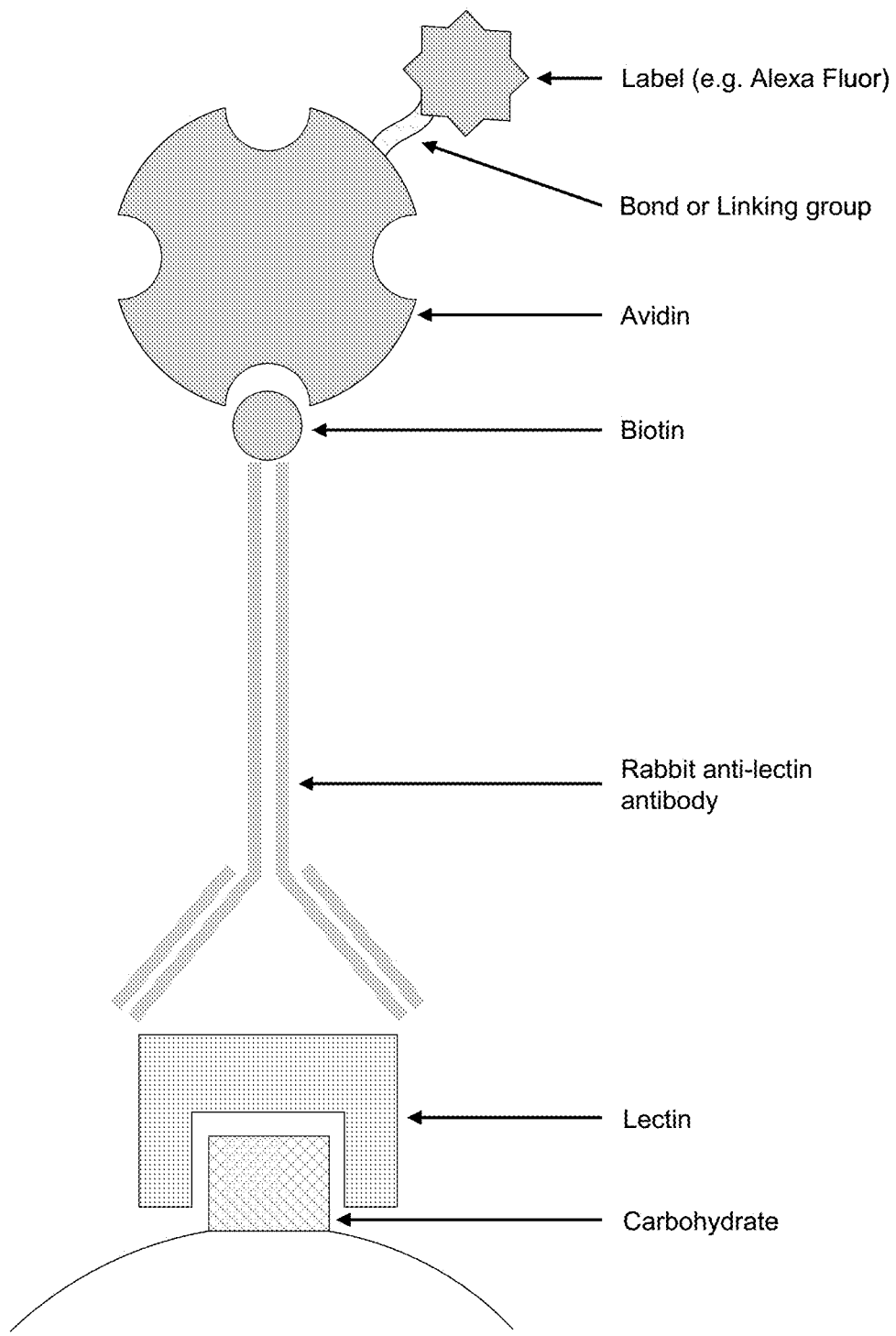
FIG. 5 is a schematic drawing showing a carbohydrate moiety on the surface of potentially cancerous oral mucosa tissue bound to a lectin. The Figure further shows an attractive interaction between the lectin and an anti-lectin antibody linked to a biotin molecule, and an attractive interaction between the biotin molecule and an avidin protein covalently linked to a "Label" to facilitate visualizing the location of the lectin.

In yet other embodiments, the lectin is linked indirectly to the detection moiety through a complex that may include one or more antibodies, biotin, and an avidin protein avidin protein which is covalently bonded to a detection moiety or linked to a detection moiety through a linking group. FIG. 5 shows one such embodiment. The lectin is once again shown bound to a cell surface carbohydrate. A rabbit anti-lectin antibody is bound to the lectin, and the antibody is also bound to a biotin molecule. The biotin molecule further binds to an avidin protein linked to a fluorophore (designated the label, e.g. Alexa Fluor). Thus, the lectin is operably linked to the fluorophore.

Figure 6:
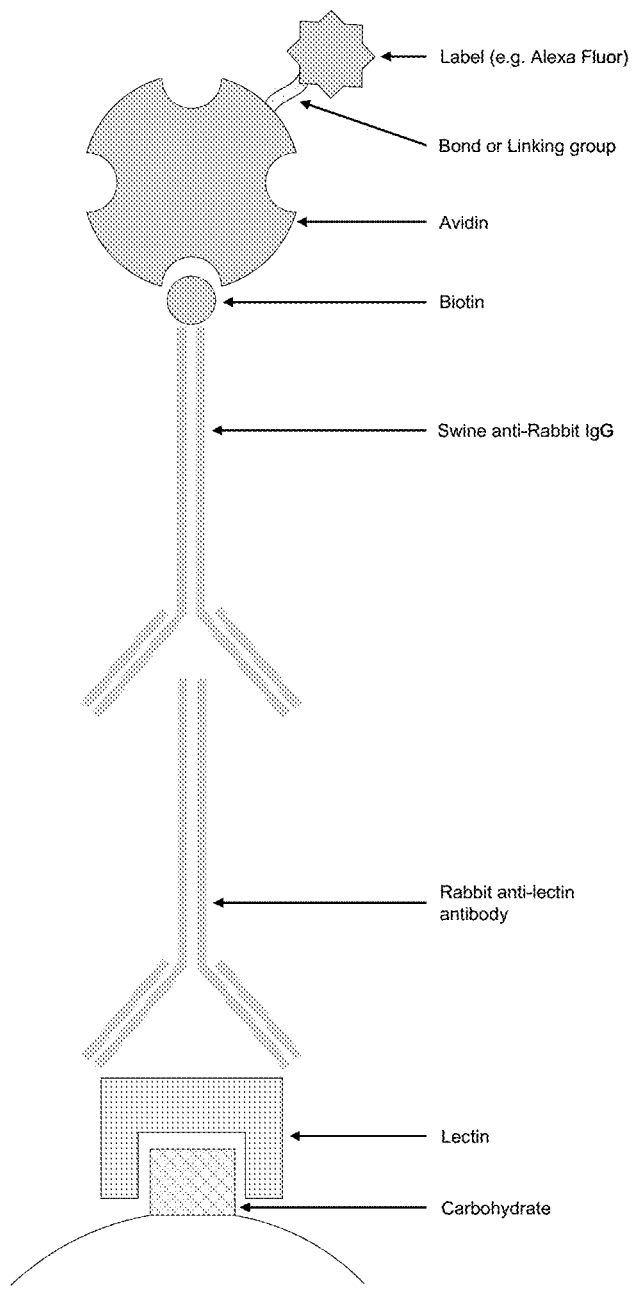
FIG. 6 is a schematic drawing showing a carbohydrate moiety on the surface of potentially cancerous oral mucosa tissue bound to a lectin. The Figure further shows an attractive interaction between the lectin and an anti-lectin antibody, an attractive interaction between the anti-lectin antibody and a second antibody linked to a biotin molecule, and an attractive interaction between the biotin molecule and an avidin protein covalently linked to a "Label" to facilitate visualizing the location of the lectin.

FIG. 6 shows yet another such embodiment. The lectin is once again shown bound to a cell surface carbohydrate. A rabbit anti-lectin antibody is bound to the lectin, and the antibody is also bound to a second antibody, a swine anti-rabbit IgG. This second antibody is also bound to a biotin molecule. The biotin molecule further binds to an avidin protein linked to a fluorophore (designated the label, e.g. Alexa Fluor). Thus, the lectin is operably linked to the fluorophore.

The composition containing the one or more lectins may be applied to the oral mucosa of the subject by any means commonly used in the art that enables delivery of the lectins to the potentially cancerous cells of the oral mucosa. Preferably, an applicator or syringe may be used to topically apply the composition directly to the oral mucosa. An applicator used in the present method could be of any type, preferably using a cotton swab or similar feature to ensure efficient complete application of the composition to the surface of the oral mucosa. Other possible methods of application include without limitation in a DMSO oral rinse, alcohol oral rinse, lotion application, in a surfactant solution, injection, and mechanical or ultrasonic agitation.

The amount of lectin to be applied to the oral mucosa is an amount wherein the differential binding of the lectin to potentially cancerous tissue can be readily visualized by conventional fluorescence imaging methods. Targeting agent concentrations may depend upon the specific type of fluorophore used, the intensity of the excitation light source, the type of lectin used, the sensitivity of the detection equipment, and other factors which may affect dosage requirements as those skilled in the art will appreciate. The quantity of lectin applied should be sufficient to overcome any background noise/binding. The concentration of lectins in the composition could range from about one nanomolar to one molar. A preferred concentration would be from about 1 to 10 micromolar, with a more preferred concentration of about 5 micromolar.

Optionally, a clinician may wish to perform various pretreatments and inspections prior to applying the composition of the present invention. For example, a pretreatment solution may be applied to the oral mucosa to accentuate the presence of the cancerous tissue. A typical solution that can be used to desiccate tissue and aid oral cancer detection is acetic acid, which has been used previously for detecting cancerous material. After the clinician applies the pretreatment solution to the gums, the clinician may visually inspect the gums with white light. Pretreatment solutions may also be used to facilitate probe binding or removal of excess glycoconjugate.

The clinician may also wish to inspect the oral mucosa upon exposure with a UV light source, optionally with the aid of an optical device, to observe any autofluorescence that may be exhibited by the tissues. This autofluorescence, or lack thereof, can help aid the clinician in the clinician's prescreening diagnosis. The optical device optionally used in such prescreening generally comprise a pair of glasses, wherein each of the lenses are designed as filters so that they will be able to pass a particular region of the visible light spectrum. For example, the excited form of cellular NAD(P)H will be observable through the optical device at the lesion site, if there are in fact cancerous tissues present on the oral mucosa. NAD(P)H is a naturally occurring molecule found within cells that is used throughout glycolysis and the citric acid cycle. This agent-reagent molecule is indicative of cellular metabolism; with accelerated cellular metabolism being one of the biochemical characteristics of cancer cells.

Once the composition of the present invention is applied to the oral mucosa, the composition is allowed to penetrate the area. The area may be gently rinsed with a solution to clear any unbound lectin present. To further clear the unbound probe, the area may be subject to serial rinses, mechanical agitation, ultrasonic agitation, swabbing or rubbing. Additionally, one or more solutions containing a substance that competitively binds to the lectin may be applied and rinsed away from the area.

The method of the invention further includes the steps of illuminating the oral mucosa with an excitation light source, and subsequently visualizing the oral mucosa to detect possible oral cancer. Light in the visual or ultraviolet range can be used as an excitation light source, however imaging of deeper tissues requires the use of near infrared (NIR) light. Hemoglobin and water, the major tissue absorbers of visible and infrared light have their lowest absorption coefficient in the NIR region around 650-900 nm. Furthermore, at longer wavelengths, light scattering by dense media is reduced, resulting in deeper penetration of excitation light into thick tissue samples. Lastly, excitation at longer wavelengths (500 nm) typically results in lower levels of tissue autofluorescence, which can drown out signals with high background noise, and decreased photochemically induced damage to the cell.

Nevertheless, since the oral cavity can be accessed easily, light does not need to penetrate several millimeters to centimeters, which allows for the use of UV, Visible, and NIR excitations. This approach is ideal in many aspects since each spectral region has its benefits as an excitation light source. For example, although NIR light can penetrate deeper, NIR light is also unobservable with the human eye, thus requiring a CCD camera (or similar high intensity camera), narrow bandpass filters, a computer and monitor to display NIR fluorescence emitted from the probe. However, UV and VIS excitation probes which emit fluorescence in the visible spectrum can greatly reduce cost, simplify imaging, and allow for more probes to be observed. Utilizing these wavelengths allows for a novel approach of viewing fluorescence with the 'naked' eye, and has been largely overlooked.

Figure 7:
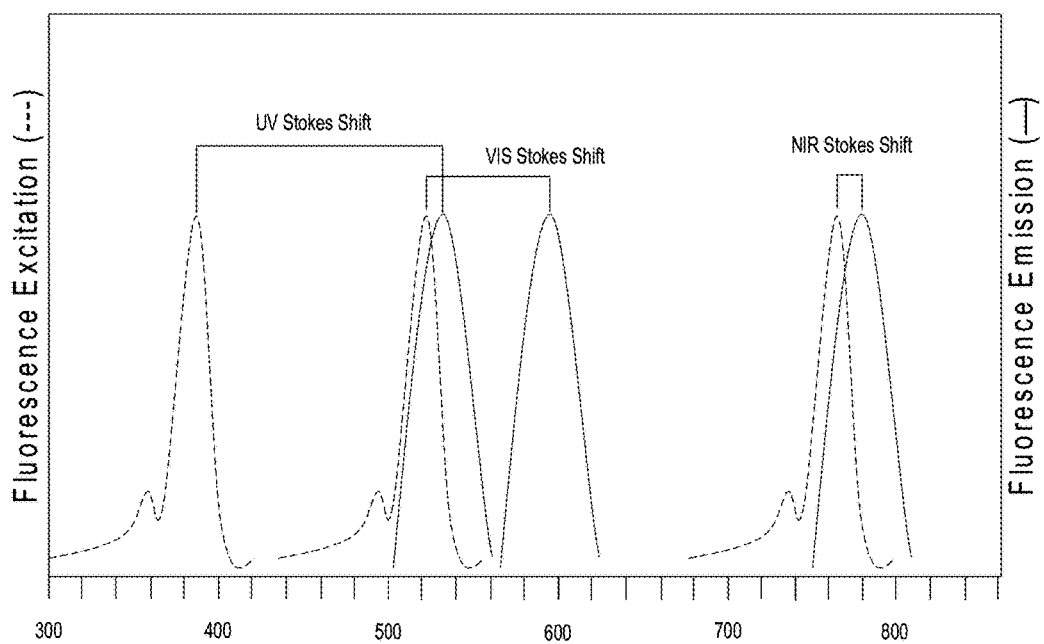
FIG. 7 shows excitation spectra and emission spectra for three exemplary fluorophores responsive in the ultraviolet (UV), visible light (VIS), and near infrared (NIR) wavelength regions. For each pair of spectra, the difference between the excitation and emission wavelengths is designated as a "Stokes shift." The magnitude of the Stokes shift increases with decreasing wavelengths of responsiveness.

Being able to resolve probes easily relies largely on the fluorophore's Stokes shift (the wavelength separation of the absorption and fluorescence maxima). When the fluorescence Stokes shift is small, it is difficult to maximize excitation and detection of the fluorophore while at the same time isolating the fluorescence emission signal from scattered excitation light. In simplistic terms, the excitation and emission sources tend to overlap (see FIG. 7, Stokes shift farthest to the right). Lower wavelength fluorophores (i.e. UV) generally have much larger Stokes shifts due to the higher energy of the absorbed photon (i.e. lower wavelength=higher energy; see FIG. 7). However, there are an increasing number of fluorophores that are commercially available that have relatively large Stokes shifts in the longer wavelength Vis and NIR spectrum which could be used in the present method, such as Alexa Fluor 430 (Invitrogen Life Science, Carlsbad, Calif.).

For multiparameter fluorescence applications, in which two or more molecular parameters are to be monitored simultaneously in the same patient, an ideal combination of probes would have strong absorption at a coincident excitation wavelength and well separated emission spectra. Likewise, a combination of probes could have strong absorption at different excitation wavelengths and well separated emission spectra. Certain UV and certain VIS excitable dyes offer such an advantage. Alternatively, overlapping emission spectra may lead the clinician to detect the two or more targeting molecules as the culmination of fluorescence of a narrow band emission.

Thus, although the method generally encompasses the use of UV, Visible light, or NIR to facilitate visualization, in one embodiment, a single excitation source in the UV is used to visualize both endogenous (NAD(P)H) and exogenous fluorophores by carefully selecting a narrow bandpass of excitation light and Stokes shifts to be able resolve signals separately via optical filtering. This method would provide a significant improvement over current methods in that multiple physiologically parameters could be visualized via the human eye, with or without appropriate filters, with a single light source, or multispectrally, without the need for additional processing equipment, which greatly reduces imaging complexity/cost and increases user compliance. Regardless, to maximize fluorescence signals, the absorption maximum of the fluorophore should be matched closely to the output wavelength of the excitation source. Preferably, the excitation source would produce a narrow band of wavelengths within the absorption maximum of the fluorophore or fluorophores used.

In certain embodiments of the method, the oral mucosa can be visualized using the naked eye. The clinician could visually detect the contrasting intensities between the excitation and emission wavelength light produced by the fluorophores that are operably linked to the lectins. Accordingly, the visually detected contrasting emission intensities would correlate to the differential lectin binding that is characteristic of cancerous tissue as compared to normal tissue, and the clinician could visually identify potentially cancerous tissue.

Preferably, the method employs one or more devices to enhance visualizing the oral mucosa. Such devices include without limitation handheld filters and filter glasses, CCD cameras, computers, image processing devices and software (i.e. normalization, background subtraction, contrast enhancements, filtration, etc.), dichroic mirrors, neutral density filters, polarizers, and microscopes. Although in certain embodiments, narrow band filters are used in the method, any combination of shortpass, longpass, notch, or bandpass filters, dichroic mirrors, neutral density filters, and polarizers could also be used to enhance visualizing the oral mucosa. Such optical devices could be incorporated as flip down filters on glasses for viewing multiple wavelengths. In certain embodiments, the excitation light source and a means for collecting the emission light for visualization are incorporated into a single handheld device, preferably containing a dichroic mirror for blocking the return of the reflected excitation light. Such a device could optionally include a dental curing light or other dental devices primarily using light for procedures.

In some embodiments, the method encompasses additional steps for further processing the optical signals from the oral mucosa to facilitate more precise and accurate detection of oral cancer and the outer margins of the oral cancer. Such additional steps may, for example, provide more accurate guidance for surgical excision of the cancerous tissue. Such additional steps may include, without limitation, taking additional pre and post contrast optical measurements, normalizing the optical measurements, comparing the results to a patient bank of normal values, and determining a patient's normal fluorescence in a region of interest. In certain embodiments, the method includes the additional step of using mathematical processing software to further analyze the optical data obtained in the method. However, image processing may not be needed to detect surgical margins. For example, all images acquired in the Example study discussed below are displayed without any processing, and surgical margins are readily apparent.

Although the present method has been discussed as it relates to the detection of cancers of the oral mucosa (oral cancers), it is recognized that cancers of epithelial mucosal tissues in general share common attributes with cancers of the oral mucosa. Accordingly, the invention further encompasses methods of detecting other cancers and precancers of the mucosa, including without limitation cervical and esophageal cancers.

In a second aspect, the invention encompasses a method for assessing the presence of oral cancer in a subject wherein the detection moiety and/or other parts of the lectin complex are applied to the oral mucosa in a separate step from applying the lectins to the oral mucosa. In this aspect, one step of the method involves applying a lectin to the oral mucosa of a subject. As in the other aspects of the invention, the lectin used in the method is one that specifically binds to one or more cell surface monosaccharide and/or oligosaccharide moiety. Preferred targets include one or more of a β-galactoside, an α- or β-N-acetylglucosamine, or a sialic acid moiety.

Preferably, the invention employs one or more lectins selected from the group consisting of Con A, LcH, VFA, PSA, GS-II, WGA, DSA, LEA, STA, LAA, OSA, PWM, PWA, UEA-II, UDA, PTA, HAA, VAA, Allo A, ABA, APA, PNA, CSA, TKA, RCA-I, RCA-II, ECA, CAA, SNA, MAA, LFA, LPA, HMA, and CCA. More preferably, the one or more lectins are selected from the group consisting of GS-II, WGA, PNA, VAA, Allo A, ABA, APA, CSA, TKA, and RCA-I. Most preferably, the lectins used are one or more of GS-II, WGA, and PNA.

This aspect additionally includes the step of applying either an antibody or an avidin molecule to the oral mucosa of the subject. The antibody or avidin applied in this step is linked to a fluorophore, either by covalent bonding or by the covalent bonding of the fluorophore and the antibody or avidin molecule to a common linking group (see upper part of the complexes shown in FIGS. 2-6).

In embodiments where an antibody linked to a fluorophore is applied to the oral mucosa of the subject, the antibody is preferably an anti-lectin antibody. An exemplary lectin complex formed by such an embodiment is shown in FIG. 2. Optionally, such embodiments may include the additional step of applying a second antibody or other targeting/complex molecule to the oral mucosa of the subject, wherein the second antibody or other targeting/complex molecule is linked to a fluorophore. The second antibody may form part of an indirect link between the lectin and the fluorophore, as shown in FIG. 3.

If the tetrameric protein avidin linked to a fluorophore is applied to the oral mucosa of the subject, the avidin must be operatively linked to the lectin to effectively visualize the lectin bound to the oral mucosa of the subject. Avidin strongly binds to biotin, a water-soluble B-complex vitamin. The biotin in turn may bind directly to the lectin to operably link the lectin and fluorophore. The resulting lectin complex is shown in FIG. 4.

Optionally, such embodiments may further include the step of applying one or more antibodies that are not linked to a fluorophore to the oral mucosa of the subject. Preferably, at least one of the antibodies that are not linked to a fluorophore is an anti-lectin antibody. In such embodiments, the antibody or antibodies may indirectly link the lectin and the biotin-bound avidin protein, thus operably linking the lectin to the fluorophore. Two exemplary lectin complexes formed by practicing the steps of this embodiment are shown in FIGS. 5 and 6.

This aspect of the invention further includes the steps of exposing the oral mucosa of the subject to excitatory light in the near infrared, visible light, or ultraviolet spectrum, and visualizing the oral mucosa to detect possible oral cancer. These steps are explained in further detail above.

In a third aspect, the invention encompasses compositions and devices assembled into a kit for detecting oral cancer. The kit provides the clinician with the needed materials to practice the methods outlined above. The kit includes one or more lectins operably linked to a detection moiety, wherein the lectins specifically bind to one or more cell surface monosaccharide and/or oligosaccharide moiety. Preferred targets include one or more of a β-galactoside, an α- or β-N-acetylglucosamine, or a sialic acid moiety. Preferably, the one or more lectins are selected from the group consisting of Con A, LcH, VFA, PSA, GS-II, WGA, DSA, LEA, STA, LAA, OSA, PWM, PWA, UEA-II, UDA, PTA, HAA, VAA, Allo A, ABA, APA, PNA, CSA, TKA, RCA-I, RCA-II, ECA, CAA, SNA, MAA, LFA, LPA, HMA, and CCA. More preferably, the one or more lectins are selected from the group consisting of GS-II, WGA, PNA, VAA, Allo A, ABA, APA, CSA, TKA, and RCA-I. Most preferably, the lectins are one or more of GS-II, WGA, and PNA. Preferably, the detection moiety is a fluorophore.

The lectin probes may be provided either in solution or in lyophilized form. If the probes are provided in the form of a lyophilized powder, the kit may additionally include a buffered solution for reconstituting the lectin. If the probes are provided in solution, the solution is preferably a buffered solution such as phosphate buffered saline (PBS). The solution may further contain a preservative such as sodium azide to facilitate long term bacteriostatic and fungistatic storage.

The kit further includes one or more light sources emitting light in the ultraviolet, visible, or near infrared spectrum. Optionally, the light source(s) may be handheld light source(s). Each light source may emit a single excitation wavelength, or may emit multiple wavelengths. The light source(s) may emit wavelengths that excite endogenous emission from NAD(P)H, preferably between 330 nm and 380 nm, more preferably, 365 nm±5 nm. The light source(s) may also provide light having the excitatory wavelength of the fluorophore, which causes the fluorophore to emit light of a characteristic emission wavelength for easily visualizing the location of the lectin.

As non-limiting examples, in one embodiment, the light provided by the light source capable of exciting the emission of an exogenous UV probe would be between 330 nm and 380 nm, preferably 365 nm±5 nm. In another embodiment, the light provided by the light source capable of exciting the emission of an exogenous NIR probe would be between 600 nm and 900 nm, preferably 630 nm±5 nm.

The kit optionally includes one or more narrow bandpass or longpass filters for visualizing the light emitted by the fluorophores and/or the endogenous fluorescence sources. The filters may be incorporated into an optical device adapted for a viewer's use, as lenses are incorporated into a pair of glasses. For visualizing NAD(P)H fluorescence, an exemplary bandpass filter would be centered at 450 nm±20 nm. For visualizing UV probe fluorescence, an exemplary bandpass filter would be centered at 450 nm±5 nm. For visualizing IR probe fluorescence, an exemplary bandpass filter would be centered at 670 nm±5 nm or 680 nm±5 nm. A longpass filter could also be included for these applications.

In certain embodiments, the kit may include the excitation light source and a means for collecting the emission light for visualization in a single handheld device, preferably containing a dichroic mirror for blocking the return of the reflected excitation light. Such a device could optionally include a dental curing light.

The kit may optionally include other devices and compositions. Non-limiting examples of additional devices and compositions that may be included are one or more visual enhancer solutions, such as acetic acid solution, calcium ion detection solutions, and solutions containing DNA or other nucleic acid probes; one or more solution applicators, such as a syringe or cotton swab-based device; one or more tissue penetrating agents, such as DMSO; a sterile scissors; a biopsy device, such as a punch biopsy device; a forceps; preparation pads; and bandages.

Figure 8:
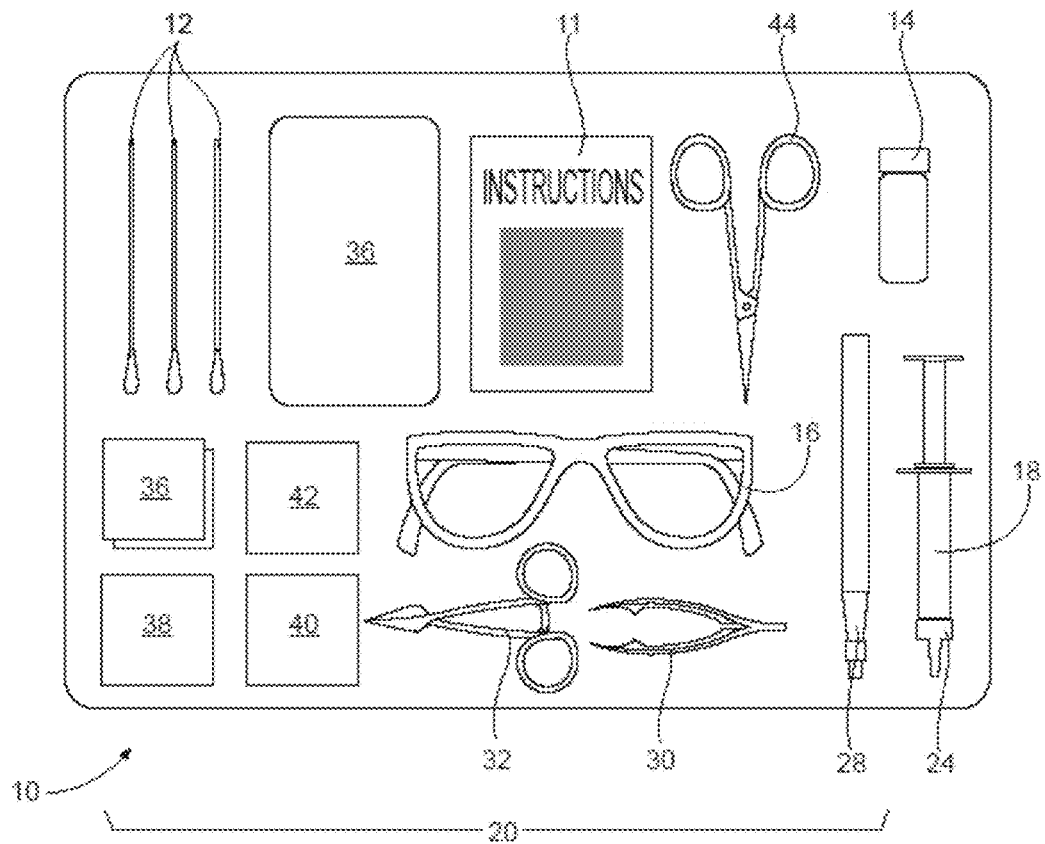
FIG. 8 depicts a kit for detecting oral cancer, including various dyeing agents, biopsy tools, an instruction manual, applicators, and glasses for viewing a band of wavelengths (i.e. optical filter).

It is contemplated that a dental practitioner will use the kit of the present invention to carry out the methods described above. As an example, FIG. 8 depicts a kit 10 for use in ascertaining whether a person may or may not have oral cancer. The kit 10 comprises some or all of a manual 11, applicators 12 for applying a visual enhancer solution 14, and an optical device 16 to assist the user in visually assessing whether or not a person may have cancer. The kit 10 can also comprise another enhancement solution 18 within a syringe 24 and a device for acquiring a sample from the patient. Such a sample-acquiring device may include without limitation a device for collecting saliva or serum or for obtaining tissue by biopsy. The kit of the present example comprises a biopsy kit 20 for further carrying out testing.

Still referring to FIG. 8, the manual 11 is a helpful tool for the diagnostic process. A common problem associated with cancer screening, particularly oral cancer screening, is overdiagnosis and unnecessary biopsy. That is, when prescreening or screening (referred to collectively as screening) is performed, many times the clinician may not properly assess whether or not the screening determines that there is the presence of cancerous tissue, often leading to false positives. Many factors can contribute to these false positives, from not being familiar with the solutions being used to enhance the cancerous tissue, to diagnosing natural permutations (i.e. aphthous ulcers, herpes simplex, etc.) as threatening, cancerous tissue. The manual 11 is a thorough manual, that contains both written and visual aids to assist the user in properly assessing cancer problems during the screening stage.

Figure 9:
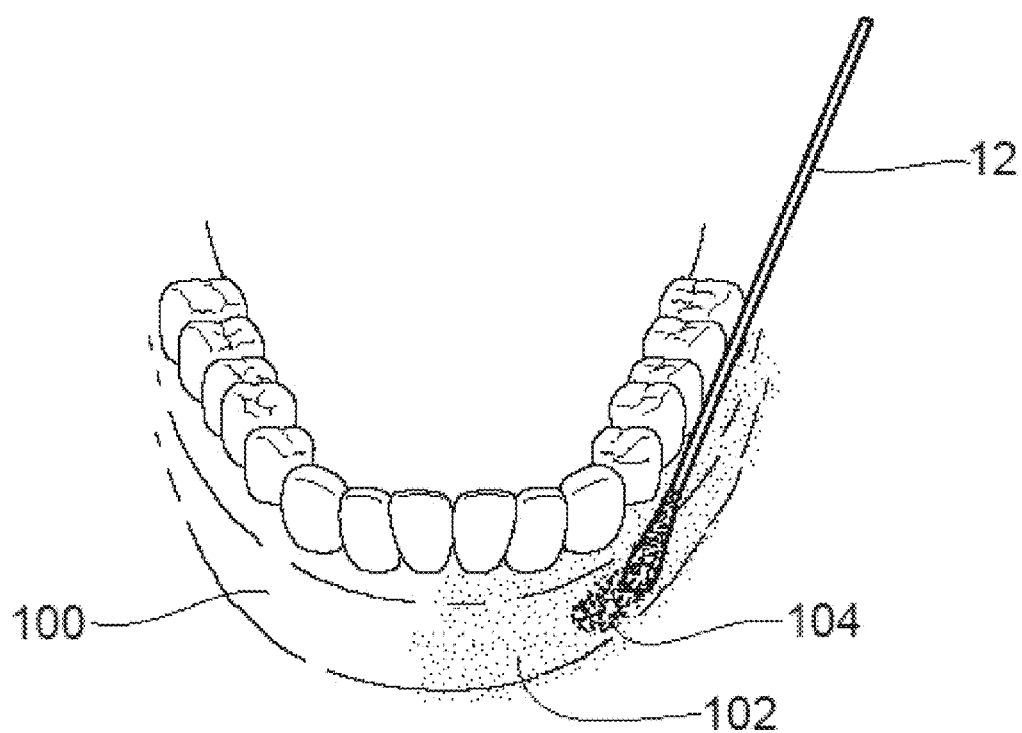
FIG. 9 depicts the application of a pre-screening fluid to a person's gums.

FIG. 9 shows the applicator 12 applying the solution 14 to a patient's gums 100 to initially detect whether or not a cancerous tissue 102 is present on the gums 100. The applicator 12 can be of any type of device, preferably using a cotton swab or similar device. The solution 14 is used to accentuate the presence of the cancerous tissue. As stated above, a typical solution 14 that can be used to desiccate tissue and aid oral cancer detection is acetic acid, which has been used previously for detecting cancerous material. After application of the solution 14 to the gums, the user will visually inspect the gums 100 with white light.

Figure 10:
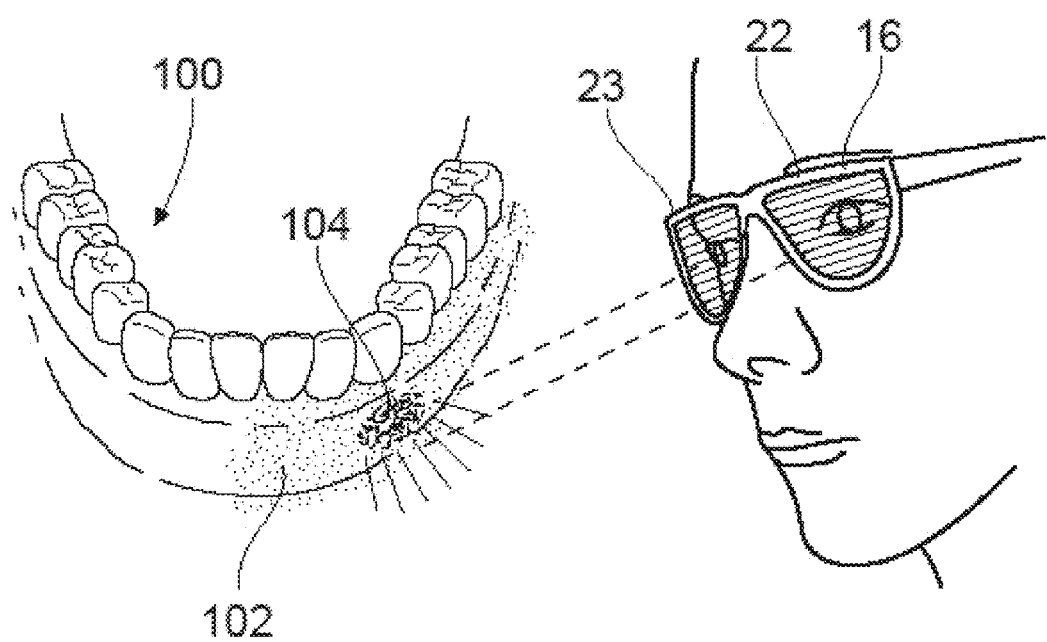
FIG. 10 shows a person using filtered viewing glasses to determine possible areas of oral cancer.

The user may also wish to inspect the gums 100 with the aid of the optical device 16 and a UV light source 28 to observe autofluorescence, as shown in FIG. 10. This autofluorescence, or lack thereof, can help aid the clinician in their prescreening diagnosis. As observed, the optical device 16 generally comprises a pair of glasses, wherein each of the lens 22, 23 are designed as filters so that they will be able to pass a particular region of the visible light spectrum. As discussed above, the excited form of cellular NAD(P)H will be observable through the optical device 16 at the lesion site, if cancerous tissues are present on the gums.

Preferably the optical device 16 is arranged so that the lenses 22 and 23 optimize the visual fluorescence of NAD(P)H and other naturally occurring tissue fluorophores, which has a strong absorption peak at 350 nm (UV) and emission peak at 450 nm (blue). As such the emission would be observable through blue longpass and/or band pass filters transmitting light above 430 nm. Furthermore, the handheld illumination device 28 would produce wavelengths tuned to the excitation maxima of NAD(P)H (i.e. 300-410 nm) and other natural tissue fluorophores. It should be understood that the shown optical device 16 is merely exemplary of possible devices used for visually enhancing potentially cancerous material. It should be understood that proper protection of both patient and clinician is advisable to avoid subjecting either to tissue-damaging UV radiation for extended periods of time.

Figure 11:
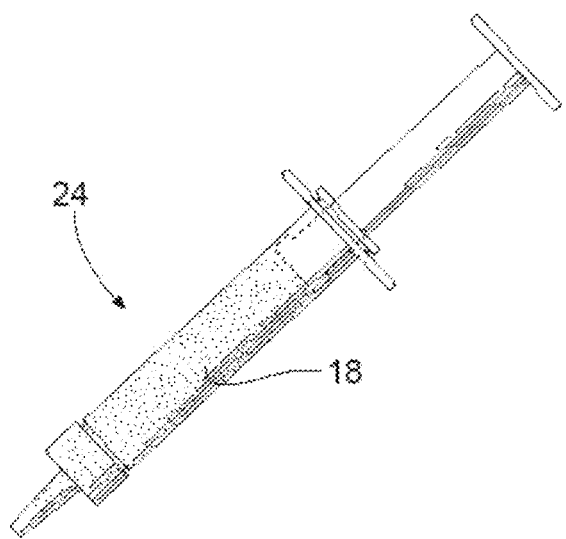
FIG. 11 shows a syringe containing a dye used to enhance the visualization of cancerous tissue.

Once prescreening has been accomplished, further testing may be necessary. FIG. 11 shows a syringe 24 that contains the second enhancement solution 18, which will be delivered to an oral cavity. The syringe 10 is demonstrative of various devices that can be used to deliver the solution 18. As an example, the solution 18 could consist of lectins conjugated with a detection moiety such as a fluorophore, but could additionally include Hoechst 33342, Hoechst 33258, DAPI, Fluoro-Gold, FURA 2-AM, Calcein Blue-AM, Indo-1-AM, antibodies, specific binding proteins, or enzyme/protease activatable probes, or any combination thereof.

The dyes used for identification and detection that comprise the solution 18 in the present invention are dyes that are not commonly used in oral screening and detections systems. Toluidine blue-O and tellurium chloride (TeCl) are the standards currently used in oral cancer screening systems. The present invention will not use these dyes for detection, but rather will employ dyes which bind to cell surface receptors (i.e. lectins conjugated to a fluorophore).

Figure 12:
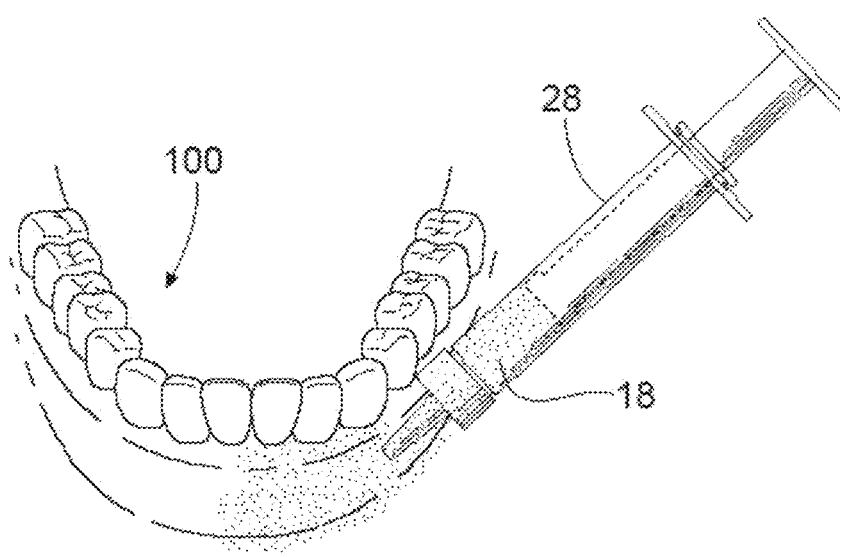
FIG. 12 shows the dye within the syringe of FIG. 11 being applied to a person's gums.
Figure 13:
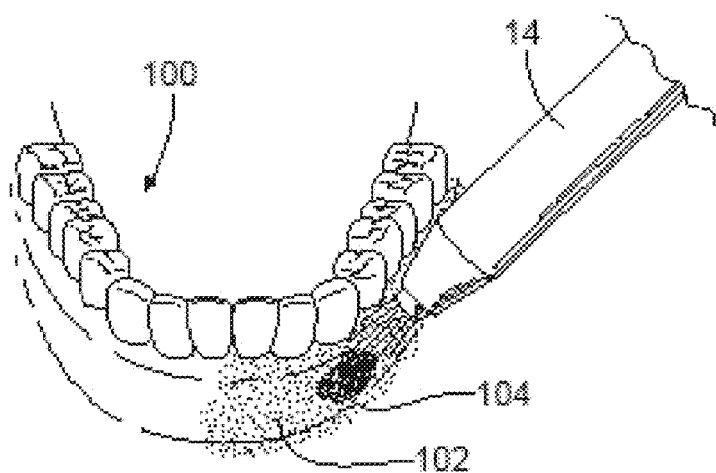
FIG. 13 shows an excitation light source, which could be a UV (Ultra Violet) light source, being used to further enhance the visualization of cancerous tissue.

FIG. 12 shows the gums 100 being tested for potential cancerous material. The solution 18 is applied to the potentially cancerous area 102 and the solution 18 is allowed to penetrate the area 102. Once the solution 18 is applied to the area 102, the area 102 will be illuminated with an excitation light source, ex: ultraviolet light source 26. If there is potentially cancerous tissue, the tissue 104 will become apparent, as the solution 18 will color the tissue 104 differently by means of fluorescence than the rest of the area 102.

As with the prescreening process, the visualization of the cancerous tissue 104 can be enhanced through the use of additional solutions 18 that contain UV excitable DNA intercalating/binding stains and/or intracellular ion detection dyes. These dyes will be suspended in solution at pre-fixed concentrations and can be applied on the potentially cancerous area 102, either using the syringe 24 or one of the applicators 12, which will significantly aid in the visualization, detection, and eventual resection of an oral lesion. Because these specific dyes accentuate the nuclear material (i.e. DNA) that is present, it makes it easier to identify cancerous material, as an increased level of nuclear material is an indication of cancers. Furthermore, the ion flux (i.e. calcium) within the intercellular pathways occurs more often for rapidly proliferating cell types (i.e. cancers), and the discussed solutions will be used to enhance these cellular components.

As discussed previously, the visual enhancement solution 18 may additionally include different molecular probes, such epidermal growth factor (EGF) for binding to a epidermal growth factor receptors (EGFR) to create a targeted fluorescent marker, sugar bonding proteins, other lectins, and/or enzyme/protease activatable probes, or other probes and receptors as noted above.

Once the tissue 104 is detected, the biopsy kit 20 of FIG. 8 is used for removal. The biopsy kit 20 comprises a punch biopsy device 28, sterile scissors 32 and 44, forceps 30, prep pads, including iodine 40 and alcohol prep pads 42, sterile fabric for application to the gums 100, such as gauze 36 and bandages 38. Other items, such as needle holders or other devices to assist in the removal of the tissue 104 can be included in the biopsy kit 20, and the kit 10, in general.

Figure 14:
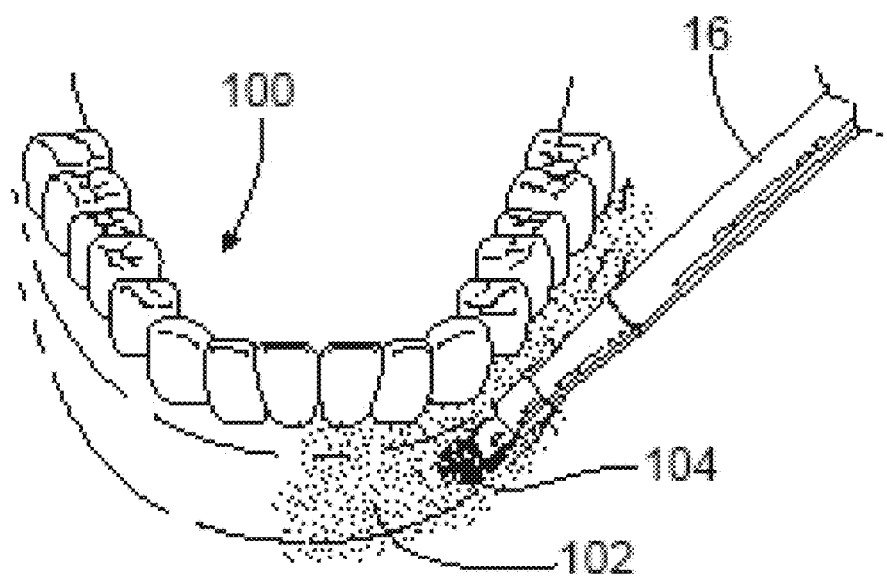
FIG. 14 is yet another step in using the oral cancer detection kit of the present invention, wherein a biopsy device is used to remove a sample of cancerous tissue.

FIG. 14 shows the punch biopsy device 16 (corresponding to 28 in FIG. 8) being used to remove the tissue 104. Once the tissue 104 is removed from the area 102, it will be delivered to a lab for analysis. The punch biopsy device 16 (corresponding to 28 in FIG. 8) can be of any standard punch device as used and known in the industry.

Figure 15:
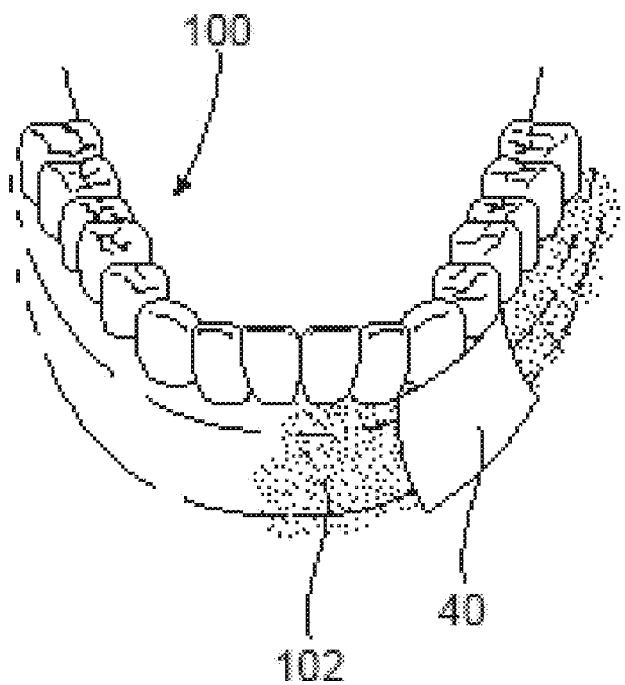
Figure 16:
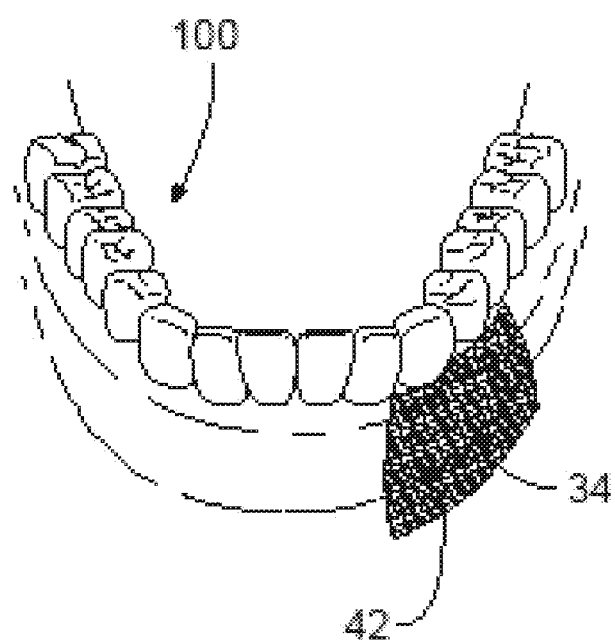
FIG. 16 shows the person's gums of FIG. 15 being treated with bandages and gauze material.

FIGS. 15 and 16 show the preparation and treatment of the gums 100 after the tissue 104 has been removed from the gums 100. In FIG. 15, the gums 100 are being prepared with either the iodine prep pad 40 or the alcohol pad 42. FIG. 16 shows application of the gauze 36 and the bandage 38 to the gums 100 to staunch bleeding, promote healing, and prevent infection where the tissue 104 was removed.

The present invention provides an improved cancer detection system by providing methods, devices, and kits that are more capable of detecting possible cancerous tissue. Previous testing systems were not inclusive, as it was not known that the added levels of testing would significantly increase detection rates, more so than a simple additive effect. As such, the present invention provides a cancer detection system that greatly enhances the ability to determine whether a person has cancerous or potentially cancerous material. Furthermore, the present invention further assists the user in properly detecting cancerous materials, by providing the manual 12 that provides both textual and pictorial information to assist the user in detecting the cancerous material The kits and methods of the invention are capable of detecting molecular level changes before detectable anatomical changes occur, providing hope of earlier cancer detection.

Although the kits of the prevent invention have been discussed as they relate to the detection of cancers of the oral mucosa (oral cancers), it is recognized that cancers of epithelial mucosal tissues in general share common attributes with cancers of the oral mucosa. Accordingly, the invention further encompasses kits for detecting other cancers and precancers of the mucosa, including without limitation cervical and esophageal cancers.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

The invention will be more fully understood upon considering the following non-limiting Example.

Example

Using Lectin-Fluorophore Probes to Differentiate Normal and Neoplastic Mucosal Tissues The inventors here report the results of clinical studies using the methods of the present invention. Specifically, the inventors have collected data from fluorescence imaging of oral mucosa tissue specimens from 11 patients. Fluorescence imaging was performed (1) using conventional tissue autofluorescence, and (2) after applying lectin-fluorophore conjugates to the surface of the tissue. Fluorophore conjugates were used containing the lectins PNA, WGA, and GS-II. Data collected from 9 of the 11 patients demonstrate that aberrant glycosylation changes can be pinpointed via fluorescent lectin conjugates, resulting in high resolution imaging of normal and cancerous tissue in the oral mucosa. Furthermore, these glycosyl changes can differentiate normal, dysplastic, and malignant tissues in the oral cavity with high contrast. This technique holds promise as a non-invasive screening method for premalignant and malignant mucosal tumors, as well as a method for defining surgical margins and monitoring cellular changes over time.

Materials and Methods

Topical Application of Lectin Probe.

Freshly extracted tissue samples were obtained either from patients diagnosed with oral cancer or from scalpel biopsies acquired from patients suspected of having oral cancer. To assess differential binding specificity between normal and cancerous tissue, biopsies of both clinically normal and abnormal oral tissues were obtained. Paired biopsies of clinically normal and abnormal oral mucosa were acquired according to accepted clinical practice. Normal tissue biopsies either came from tissue adjacent to the surgical margin or from a slight extension of suspicious lesion margins.

Upon extraction, tissue samples were placed in 1× phosphate buffered saline (PBS) (Sigma Aldrich, Milwaukee, Wis.) to prevent dehydration and then were immediately imaged. In short, epi-illumination (reflectance) images were acquired from the tissue samples under narrow band illumination of UV light for autofluorescent measurements of nicotinamide adenine dinucleotide phosphate (NADPH) and other natural intrinsic fluorophores, and under narrow band illumination of near-infrared light for autofluorescent/pre-incubation measurements corresponding to the excitation wavelength of Alexa Fluor 647 (Invitrogen, Carlsbad, Calif.). Both measurements were taken before topical application of Alex Fluor 647 lectin conjugates (Invitrogen, Carlsbad, Calif.) to obtain a comparison of signals originating from tissue autofluorescence at 365 nm and 630 nm.

To investigate whether the binding pattern of Alexa Fluor 647 lectin conjugates differed in normal and neoplastic oral tissues, high-resolution fluorescence imaging of topically labeled fresh clinically normal and abnormal oral biopsies was carried out. Specifically, Alexa Fluor 647 lectin conjugates (5 µM titration in 1×PBS, pH 7.4) were topically applied to these tissue samples in the presence of 10% dimethylsulfoxide (DMSO) (Sigma Aldrich, Milwaukee, Wis.). DMSO was used as a permeation enhancer to improve delivery of the Alexa Fluor 647 lectin conjugates through the epithelium of these tissue samples. The lectin conjugates studied in this investigation were WGA (*Triticum vulgare*), GS II (*Griffonia simplicifoia*), and PNA (peanut lectin), which are specific for N-acetyl Glucosamine & Sialic acid residues, N-acetyl Glucosamine resides, and Galactose & desialiated glyco residues.

Only one lectin conjugate was applied to each paired sample set. If additional tissue was available, multiple probes were investigated with the same patient. Samples were incubated with Alexa Fluor 647 lectin conjugates for 60 minutes, washed with 3 serial dilutions of 1×PBS, with the first wash consisting of a 10% DMSO in 1×PBS to ensure unbound dye was removed, and imaged using a custom wide-field fluorescence imaging system with appropriate excitation and emission filters. Because of the wide field of view (~5 cm×5 cm for the custom optical system), wide-field imaging was used to survey the tissue. Appropriate control experiments were performed to standardize the custom optical system. Paired sets of biopsies were imaged together to ensure they received matched imaging conditions (i.e. detector gain and radiant illumination power). All tissue was made available for both frozen section and hematoxylin and eosin (H&E) staining.

Optical System.

Figure 17:
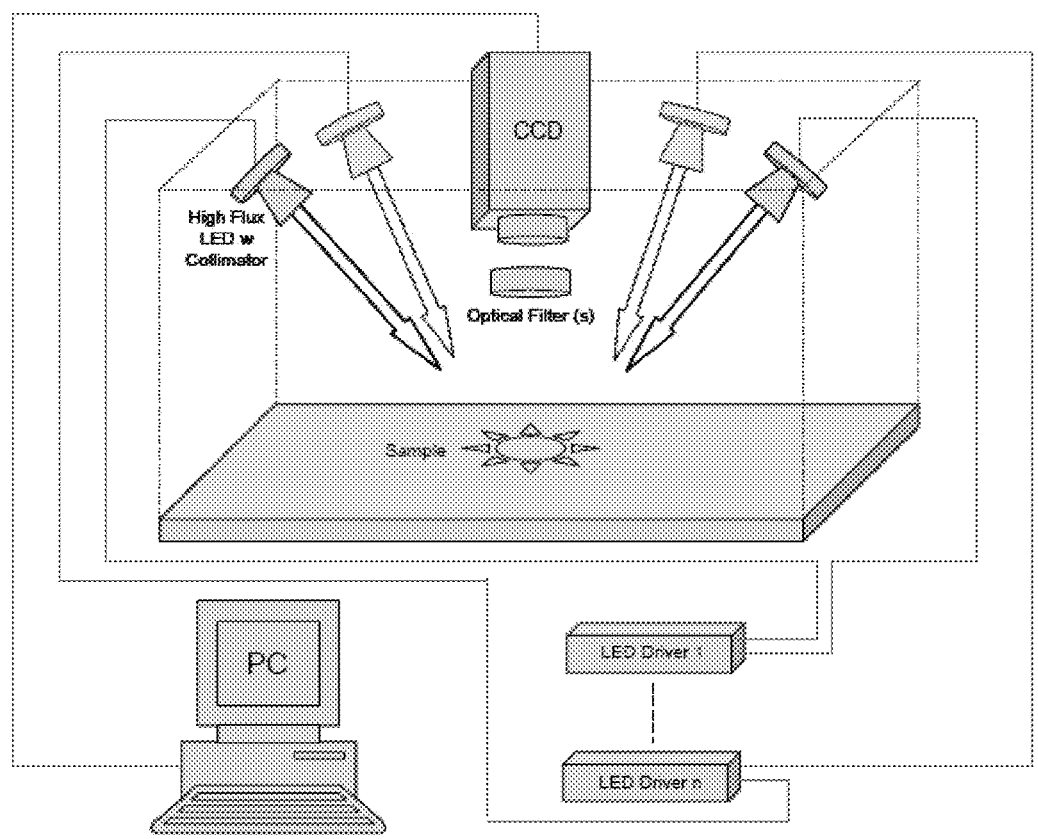
FIG. 17. is a schematic drawing of a custom designed optical imaging system capable of multi-spectral epi-illumination (reflectance) imaging, which can be used in the present invention.

As stated above, following biopsy, tissue sample images were acquired using a custom designed optical system (See FIG. 17). This imaging system allows for epi-illumination data acquisition to be obtained at multiple wavelengths; specifically using white light, UV (365 nm±7.25 nm), and near infrared (630 nm±10 nm). Excitation illumination was performed with high intensity light emitting diodes (Opto Technology Inc., Wheeling, Ill.) collimated and directed to evenly illuminate the entire field of view (i.e. 5 cm×5 cm). The high intensity LEDs were powered using constant current LED drivers (LuxDrive a division of LEDdynamics Inc, Randolph, Vt.) so that constant radiant power could be achieved. Photons generated within the tissue sample were then detected by a scientific CCD camera (Coolsnap HQ, Photometrics, Tucson, Ariz.) using the appropriate bandpass filters and longpass filters (Thorlabs, Newton, N.J.). The filters for each combination are summarized in Table 3 below.

TABLE 3

Summary of Filters Used for Excitation and Fluorescence Measurements

|  | 365 nm High Flux LED | 630 nm High Flux LED |
|---|---|---|
| Excitation | 360 nm ± 5 nm bandpass | 640 nm ± 5 nm bandpass |
| Fluorescence | 400 nm longpass and<br>1. 450 nm ± 5 nm bandpass<br>2. 450 nm ± 20 nm bandpass | 650 mn longpass and<br>680 nm ± 5 nm bandpass |

Pathological Diagnosis.

Following imaging, each sample received a unique label with no patient identifying information so that the pathological diagnosis was determined independently from the fluorescent staining results. Tissue samples were fixed and frozen sections were acquired for quick initial diagnosis. However, for final pathological diagnosis, the samples were paraffin embedded and submitted for routine hematoxylin and eosin (H&E) staining and examined by a board certified pathologist.

To evaluate effects of Alexa Fluor lectin conjugate labeling on H&E staining, we compared Alex Fluor lectin conjugate labeled slices with unlabeled control slices from the same biopsy set. Comparison of these slices showed no effect of labeling on H&E, staining. Further H&E staining was similar for normal and clinically abnormal tissue independent of the degree of staining with Alexa Fluor lectin conjugate. The pathological diagnosis was then classified into one of the following 3 categories: (1) normal, (2) dysplasia and (3) cancer with stage.

Quantification of Imaging Data.

Wide-field fluorescence images of the oral tissue samples obtained before and after incubation were quantitatively analyzed using ImageJ (NIH, Bethesda, Mass.) to calculate the mean fluorescence intensity (MFI) across the tissue surface. ImageJ was also used to obtain a measure of the camera background noise, and the measured MFI's were recorded with the static background noise subtracted. To calculate a measure of binding affinity between normal and cancerous tissue, the differential signal ratio (sometimes called signal-to-noise ratio, SNR) between those samples was determined by taking the MFI value from the normal tissue and dividing it by the MFI value from the tumor tissue. However, for those samples where the PNA conjugate was used, SNR values were calculated by dividing the MFI of the tumor tissue by the MFI of the normal tissue, since the tissue type having elevated signals was the opposite for the PNA conjugate as compared to the WGA and GS II conjugates. This SNR calculation provides the most robust measure of differential binding of the lectin conjugates, since the samples were imaged together and no other manipulation of the raw values were made.

Statistical Analysis.

All statistical analyses were performed using a 95% confidence interval, which relates to a p value <0.05 being statistically significant.

Results

In the time frame allotted for this study, 11 patients were recruited for investigations of molecular imaging of oral neoplasia using fluorophore conjugated lectins. Table 4 below lists the reference number, age, and gender of the eleven patients, the lectin probes used to image the tissue specimens from each patient, and the anatomical sites and histological diagnoses of the associated clinically normal and abnormal paired biopsy sets from each patient. Two of the clinically abnormal biopsies evaluated in this study were histologically normal; two samples were resected samples containing large regions of cancerous, dysplastic, and normal cells; and 7 of the included paired samples were confirmed both clinically and histologically.

Patient 9 was excluded from the data set for several reasons: first, the abnormal biopsy came from the larynx while the normal tissue came from the base of the tongue, representing grossly different tissue morphology; second, the samples were acquired by a surgeon unfamiliar with the standards, goals, and procedures of the study; and third, we decided to focus on cancers of the oral cavity for this investigation.

TABLE 4

Summary of Paired Biopsy Sets Used in Lectin Probe Imaging Studies:

| Patient number | Gender | Age | Probe | Anatomical site | Pathological diagnosis of specimen |
|---|---|---|---|---|---|
| 1 | M | 57 | PNA | Base of Tongue: Base of Tongue | Cancer: Normal |
| 2 | M | 55 | PNA, WGA | Tongue: Tongue | Cancer: Normal |
| 3 | F | 76 | PNA, WGA | Retromoral Trigone: Cheek | Cancer: Normal |
| 4 | M | 30 | GS II, WGA | Tongue: Tongue | Cancer: Normal |
| 5 | M | 39 | WGA | Cheek | Normal |
| 6 | F | 60 | WGA | Cheek: Cheek | Cancer: Normal |
| 7 | M | 65 | WGA | Lip: Lip: Lip | Cancer: Dysplasia: Normal |
| 8 | M | 34 | WGA | Cheek: Cheek | Normal: Normal |
| 9 | M | 70 | WGA | Larynx: Base of Tongue | Excluded |
| 10 | F | 40 | WGA | Cheek: Cheek | Cancer: Normal |
| 11 | M | 52 | WGA | Tongue: Tongue: Tongue | Cancer: Dysplasia: Normal |

Autofluorescence Imaging.

The first goal of this study was to investigate the potential use of UV light excitation of NADPH and other naturally occurring intrinsic fluorophores to detect oral neoplasms. UV autofluorescence has not been used commercially, and offers several advantages, since the human eye can essentially act as the 'filter' to remove the excitation light eliminating unnecessary cost and device complexity associated with optical filtering.

Figure 18:
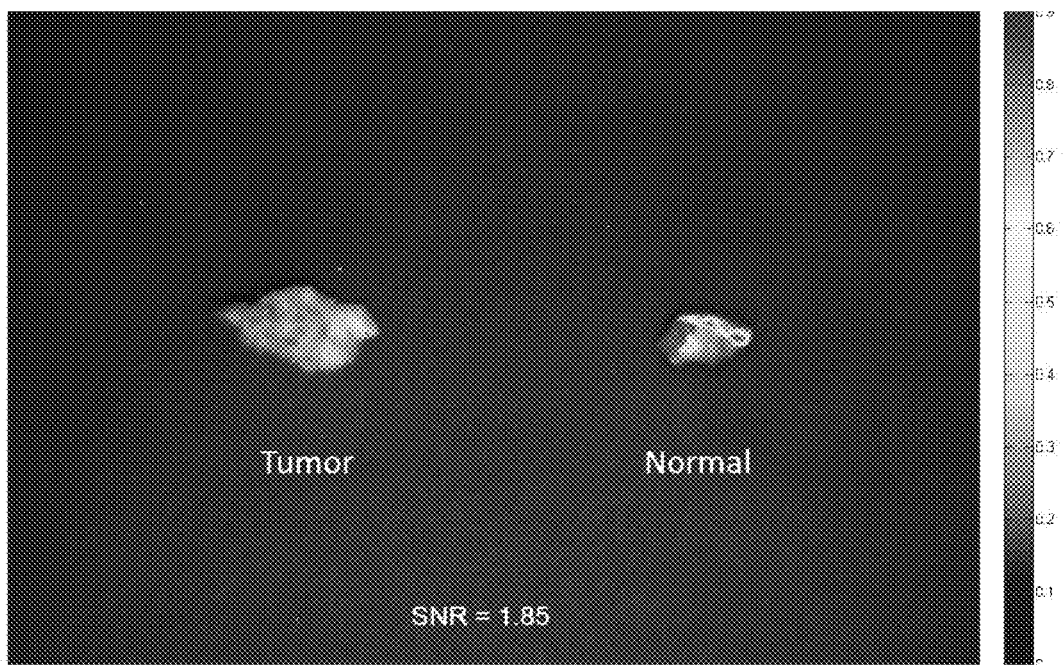
FIG. 18 is a UV autofluorescent image superimposed on the white light image of a normal and abnormal tissue biopsy set obtained from patient number 3. Image was obtained using a CCD camera with a 450 nm±20 nm bandpass filter and a 400 nm longpass filter.

We found that UV light centered at 365 nm produces signals from normal and abnormal tissues which could be distinguished. FIG. 18 shows an autofluorescence image obtained where UV light was used to cause autofluorescence in tissue samples obtained from patient number 3 superimposed on a white light image of the same tissue samples. The fluorescence intensity scale (in au) is shown to the right of the fluorescence image. The cancerous tissue sample on the left has higher fluorescence intensity than the normal tissue on the right. The calculated SNR between normal and abnormal tissue was 1.85 when the fluorescent signals were measured using a CCD camera with a 450 nm±20 nm bandpass filter and a 400 nm longpass filter. Comparable results were obtained when autofluorescent images were acquired with a 450 nm±5 nm bandpass filter and a 400 nm longpass filter; however, better contrast was consistently obtained with the first filter choice.

Similar data was obtained using autofluorescence in the other tissue samples. For patient 2, the measured differential signal ratio between normal and cancerous tissue was 1.43; for patient 4, the measured differential signal ratio was 1.38; for patient 7, the measured differential signal ratio was 1.85; for patient 9, the measured differential signal ratio was 2.05; for patient 10, the measured differential signal ratio was 1.28; and for patient 11, there was no meaningful differentiation between normal and cancerous tissue.

Autofluorescent images were also acquired by the CCD with no filtering and with the use of just the 400 nm longpass filter. Although the images captured by the system with no or just the 400 nm longpass filter show a reduction in image quality, human visualization of the samples with no optical filtering was similar to human visualization obtained by the system with the first filter choice. There is a great difference between the images acquired by the CCD camera and the human eye, since the camera sensor has a linear response (i.e. quantum efficiency) over a broad range of wavelengths and also the ability to detect wavelengths beyond the human visual system. In contrast, the human eye is more sensitive to specific wavelengths (it does not have a linear response to wavelengths) and is limited to sensing wavelengths between ~380-750 nm.

Fluorescence Imaging Using WGA Lectin Fluorophore Conjugate.

Figure 19:
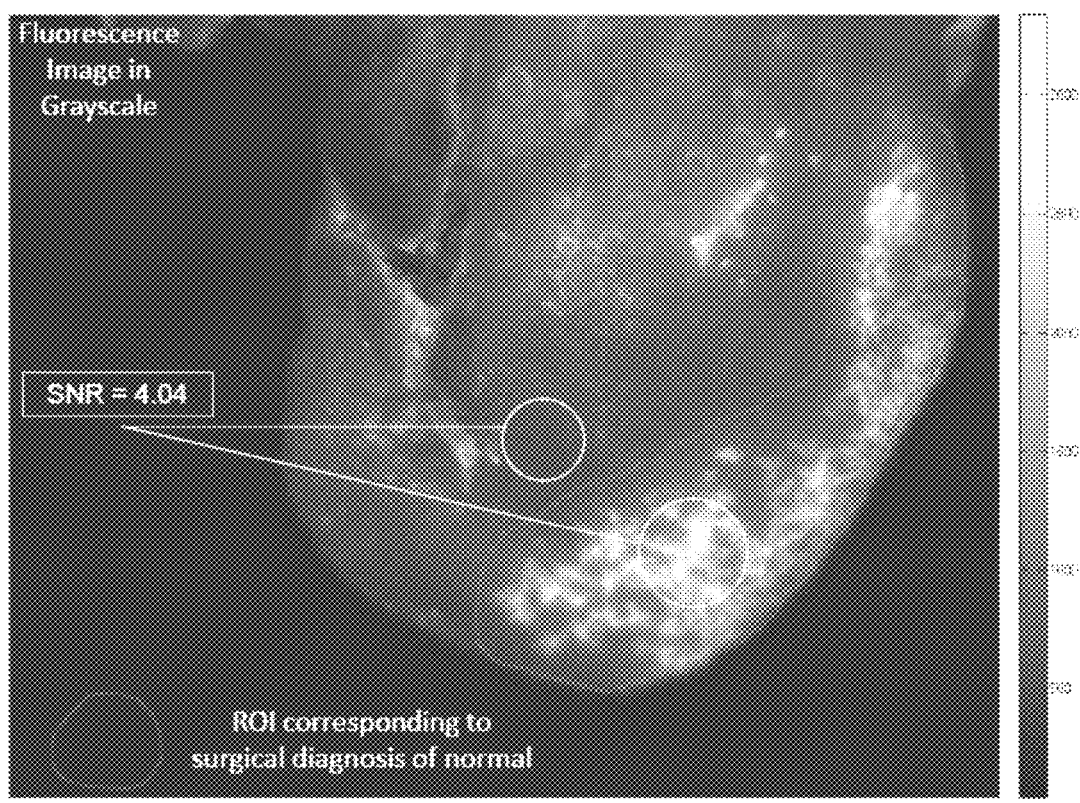
FIG. 19 is a fluorescence image of tissue obtained from patient number 2 and stained with a WGA-fluorophore probe.

A complete glossectomy (removal of the tongue) was performed on patient 2. The removed tissue was stained with 4 ml of 5 µM WGA probe in 10% DMSO solution and incubated for one hour at 37 degrees C. The tissue was then washed three times in succession, the first time with 100 ml 1×PBS in 10% DMSO, and the second and third times with 100 ml 1×PBS. The tissue was then exposed to the excitation light source, and the resulting fluorescence image is shown in FIG. 19.

The fluorescence intensity scale (in au) is shown to the right of the fluorescence image. In the fluorescence image itself, the region of interest on the lower right section of the tongue tissue inside the broken line was surgically diagnosed as normal. The rest of the tongue tissue was determined to be cancerous. As shown in the image, fluorescence intensity was substantially higher in the normal tissue than in the cancerous tissue. Based on a comparison of the fluorescence intensity measured from the cancerous tissue (within the leftmost circle) and the normal tissue (within the rightmost circle), the differential signal ratio (fluorescence intensity ratio of normal tissue to cancerous tissue) for this sample was calculated to be 4.04.

Figure 20:
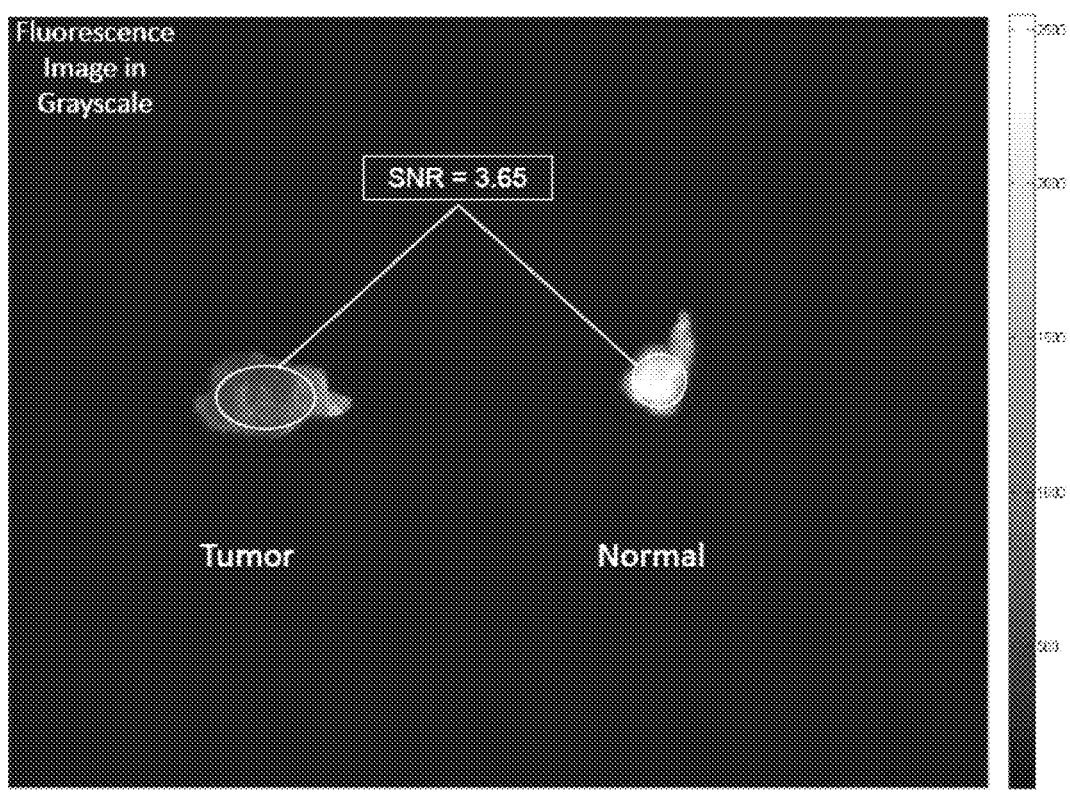
FIG. 20 is a fluorescence image of two tissue samples obtained from patient number 3 and stained with a WGA-fluorophore probe.

Both normal and tumor tissue samples were obtained by biopsy from the buccal mucosa of patient 3. The tissue samples were stained with 0.5 ml of 5 µM WGA probe in 10% DMSO solution and incubated for one hour at 37 degrees C. The tissue samples were then washed three times in succession, the first time with 40 ml 1×PBS in 10% DMSO, and the second and third times with 40 ml 1×PBS. The tissue samples were then exposed to an excitation light source, and the resulting fluorescence image is shown in FIG. 20.

The fluorescence intensity scale (in au) is shown to the right of the fluorescence image. In the fluorescence image itself, the normal tissue sample is on the right and the tumor tissue sample is shown on the left. As shown in the image, fluorescence intensity was substantially higher in the normal tissue than in the cancerous tissue. Based on a comparison of the fluorescence intensity measured from the cancerous tissue (within the leftmost oval) and the normal tissue (within the rightmost circle), the differential signal ratio for this sample was calculated to be 3.65.

Figure 21:
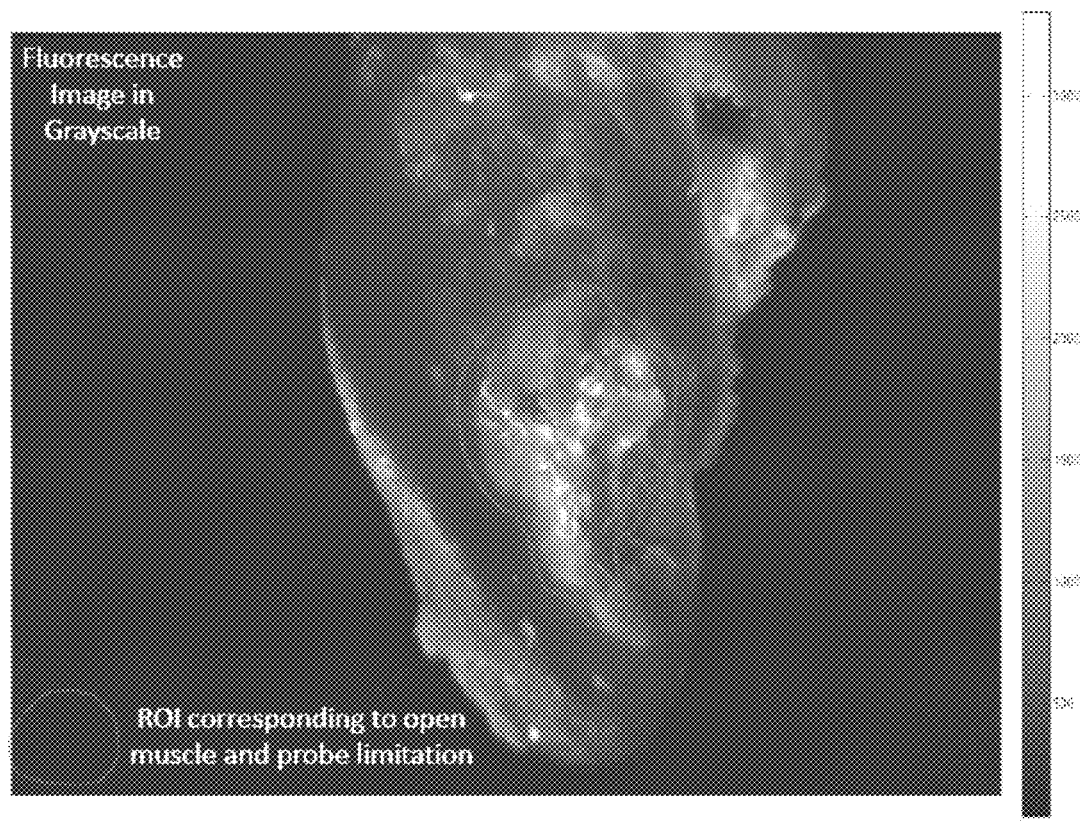
FIG. 21 is a fluorescence image of tissue obtained from patient number 4 and stained with a WGA-fluorophore probe.

A partial glossectomy was performed on patient 4. The removed tissue was stained with 4 ml of 5 µM WGA probe in 10% DMSO solution and incubated for one hour at 37 degrees C. The tissue was then washed three times in succession, the first time with 100 ml 1×PBS in 10% DMSO, and the second and third times with 100 ml 1×PBS. The tissue was then exposed to an excitation light source, and the resulting fluorescence image is shown in FIG. 21.

Figure 22:
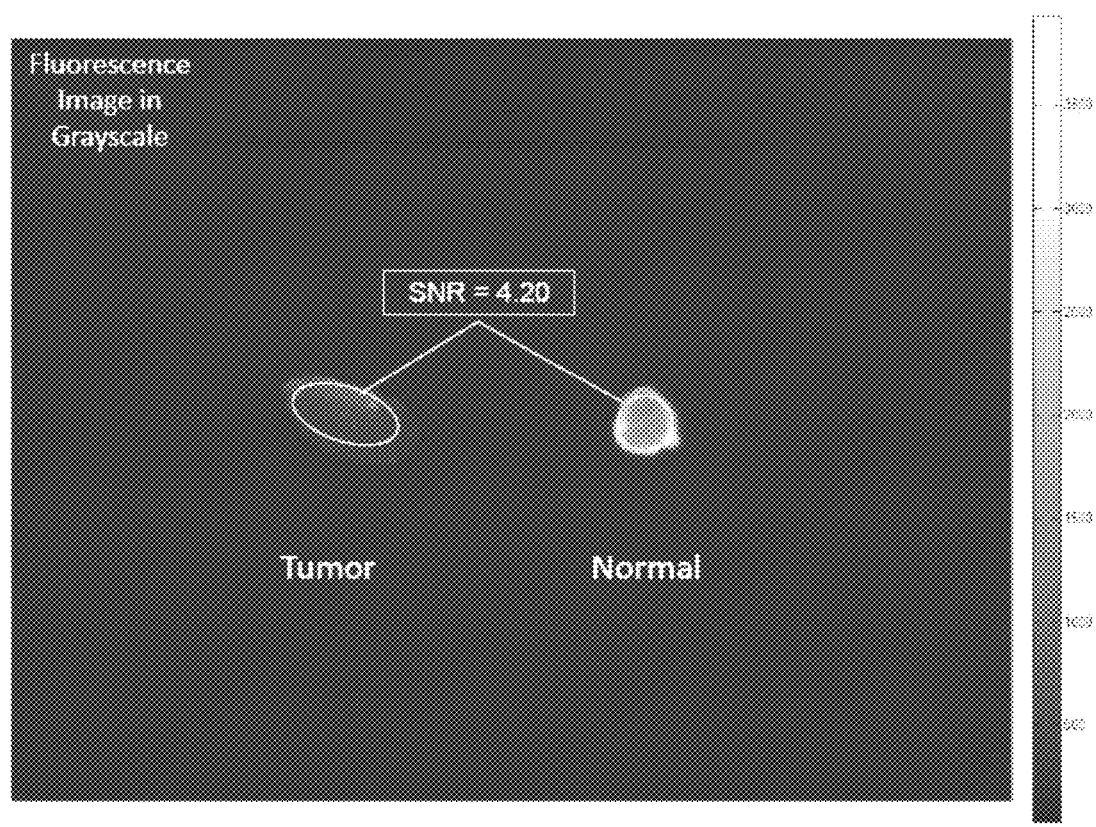
FIG. 22 is a fluorescence image of two tissue samples obtained from patient number 4 and stained with a WGA-fluorophore probe.

Both normal and tumor tissue were removed from the sample obtained by partial glossectomy, and the isolated tissues were then exposed to an excitation light source, and the resulting fluorescence image is shown in FIG. 22.

The fluorescence intensity scale (in au) is shown to the right of the fluorescence image. In the fluorescence image itself, the normal tissue is on the right and the cancerous tissue is shown on the left. As shown in the image, fluorescence intensity was substantially higher in the normal tissue than in the cancerous tissue. Based on a comparison of the fluorescence intensity measured from the cancerous tissue (within the leftmost oval) and the normal tissue (within the rightmost circle), the differential signal ratio for this sample was calculated to be 4.20.

Figure 23:
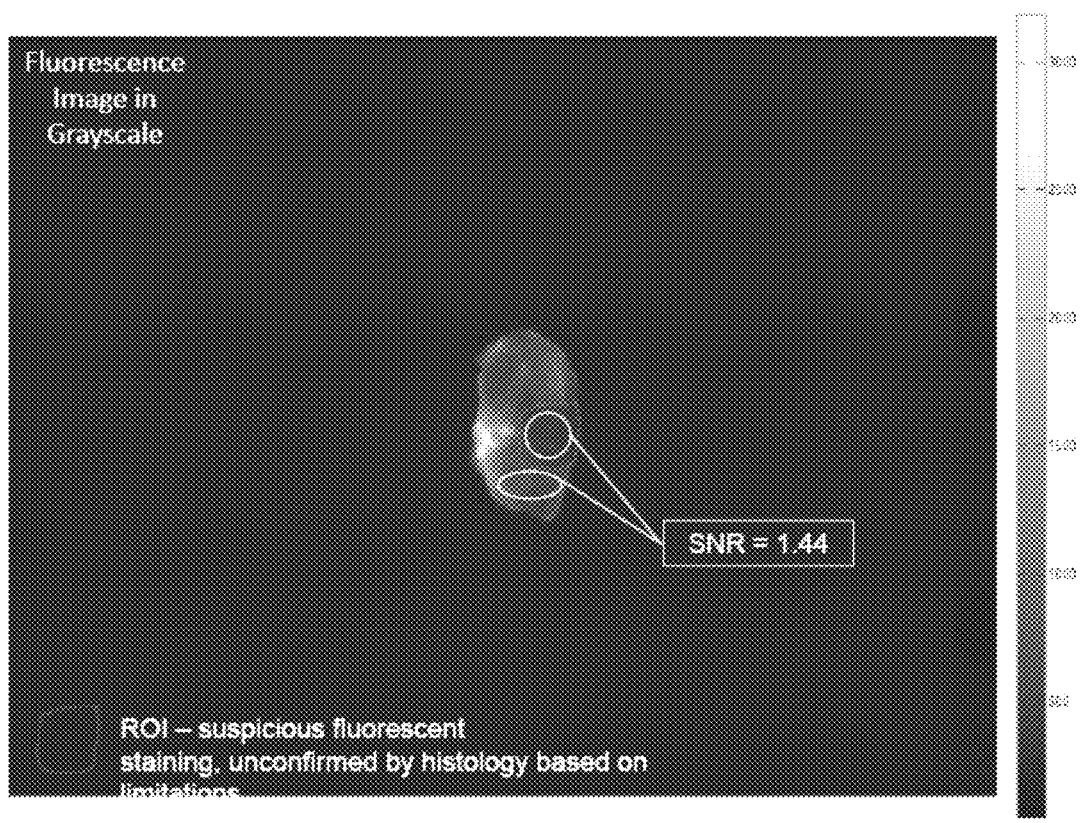
FIG. 23 is a fluorescence image of tissue obtained from patient number 5 and stained with a WGA-fluorophore probe.

A dysplastic tissue sample was obtained by biopsy from the cheek oral mucosa of patient 5. The tissue sample was histologically determined to be normal (non-cancerous). The tissue sample was stained with 0.5 ml of 5 µM WGA probe in 10% DMSO solution and incubated for one hour at 37 degrees C. The tissue sample was then washed three times in succession, the first time with 40 ml 1×PBS in 10% DMSO, and the second and third times with 40 ml 1×PBS. The tissue sample was then exposed to an excitation light source, and the resulting fluorescence image is shown in FIG. 23.

The fluorescence intensity scale (in au) is shown to the right of the fluorescence image. In the fluorescence image itself, the area of interest inside the broken line border has a significantly lower fluorescence intensity than the surrounding regions, a staining pattern that is suspiciously similar to what was seen previously in cancerous tissue. However, histology tests did not confirm the presence of cancer. This is not entirely unexpected, given that a comparison of the fluorescence intensity measured from the suspicious area of interest (within the upper circle) and the surrounding area (within the lower oval) showed a differential signal ratio of 1.44, a substantially lower differential signal ratio than was characteristic of normal/cancerous tissues in other samples.

Figure 24:
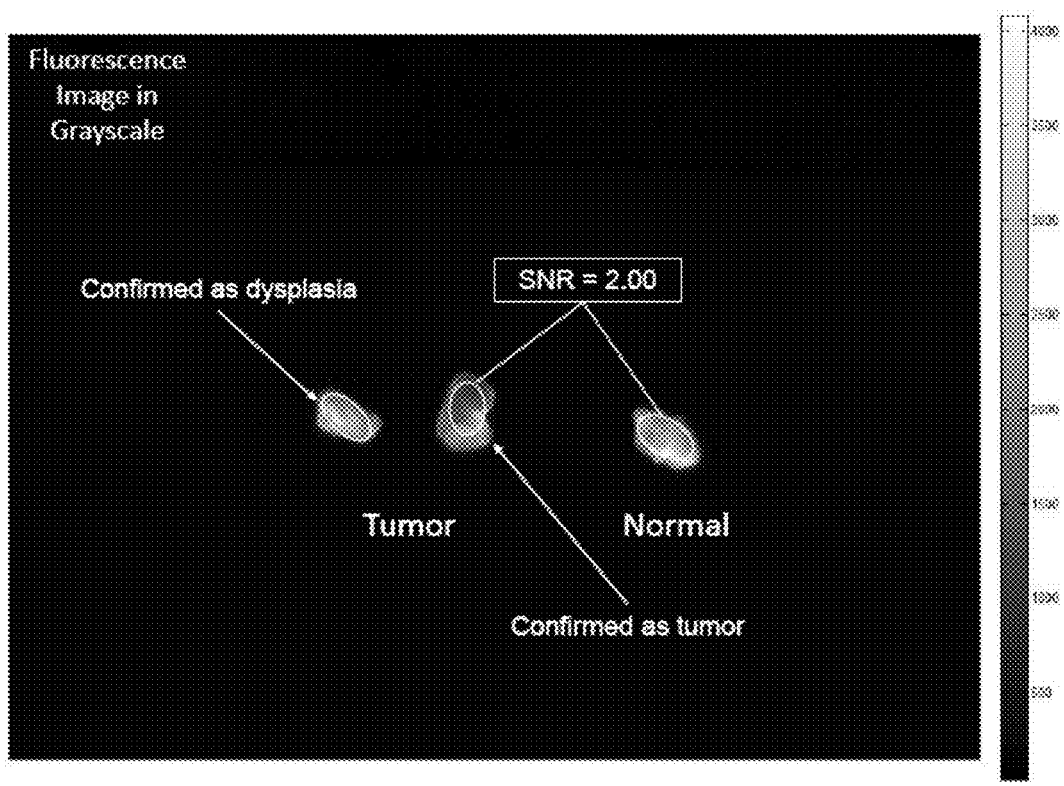
FIG. 24 is a fluorescence image of two tissue samples obtained from patient number 6 and stained with a WGA-fluorophore probe.

Normal and tumor tissue samples were obtained by biopsy from the buccal mucosa of patient 6. Histology was used to determine that one area of the tumor tissue was in fact dysplastic rather than cancerous, but that a second area in the tumor tissue sample was cancerous. The tissue samples were stained with 0.5 ml of 5 µM WGA probe in 10% DMSO solution and incubated for one hour at 37 degrees C. The tissue samples were then washed three times in succession, the first time with 40 ml 1×PBS in 10% DMSO, and the second and third times with 40 ml 1×PBS. The tissue samples were then exposed to an excitation light source, and the resulting fluorescence image is shown in FIG. 24.

The fluorescence intensity scale (in au) is shown to the right of the fluorescence image. In the fluorescence image itself, the normal tissue is on the right, the cancerous tissue is in the center, and the dysplastic tissue is on the left. As shown in the image, fluorescence intensity was substantially higher in the normal tissue than in the cancerous tissue. Based on a comparison of the fluorescence intensity measured from the cancerous tissue (within the center circle) and the normal tissue (within the rightmost oval), the differential signal ratio for this sample was calculated to be 2.00.

Figure 25:
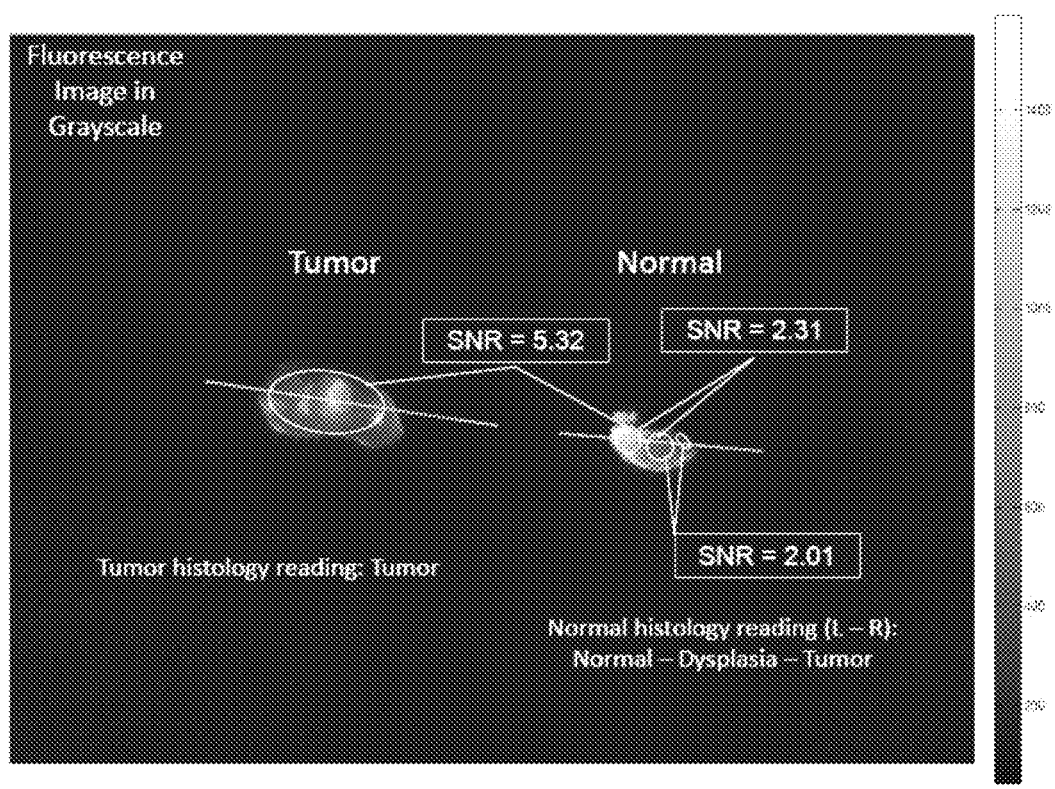
FIG. 25 is a fluorescence image of two tissue samples obtained from patient number 7 and stained with a WGA-fluorophore probe.

Normal and tumor tissue samples were obtained by biopsy from the lip of patient 7. The tissue samples were stained with 0.5 ml of 5 µM WGA probe in 10% DMSO solution and incubated for one hour at 37 degrees C. The tissue samples were then washed three times in succession, the first time with 40 ml 1×PBS in 10% DMSO, and the second and third times with 40 ml 1×PBS. The tissue samples were then exposed to an excitation light source, and the resulting fluorescence image is shown in FIG. 25.

The fluorescence intensity scale (in au) is shown to the right of the fluorescence image. In the fluorescence image itself, the "normal" tissue sample is on the right and the tumor tissue sample is on the left. Histology confirmed that the tumor tissue sample was cancerous; however, histology revealed that the "normal" tissue sample actually transitioned from normal tissue (within the leftmost circle) through dysplastic tissue (within the center circle) and finally to cancerous tissue (within the rightmost oval). As shown in the image, fluorescence intensity was substantially higher in the normal regions of the tissue samples than in the cancerous regions, with the fluorescence intensity of the dysplastic regions being intermediate between the two. Based on a comparison of the fluorescence intensity measured from the cancerous tissue (within the leftmost oval) and the normal tissue (within the rightmost oval), the differential signal ratio for this sample was calculated to be 5.32. The differential signal ratio between the dysplastic (central circle) and cancerous (rightmost oval) regions of the "normal" tissue sample was calculated to be 2.01. Finally, the differential signal ratio between the dysplastic (central circle) and cancerous (rightmost oval) regions of the "normal" tissue sample was calculated to be 2.01. This result, along with the data obtained from patient 2, demonstrates how this approach is able to spatially resolve areas of tissue which are normal, dysplastic, and cancerous; thus showing how surgical margin detection is possible.

Figure 26:
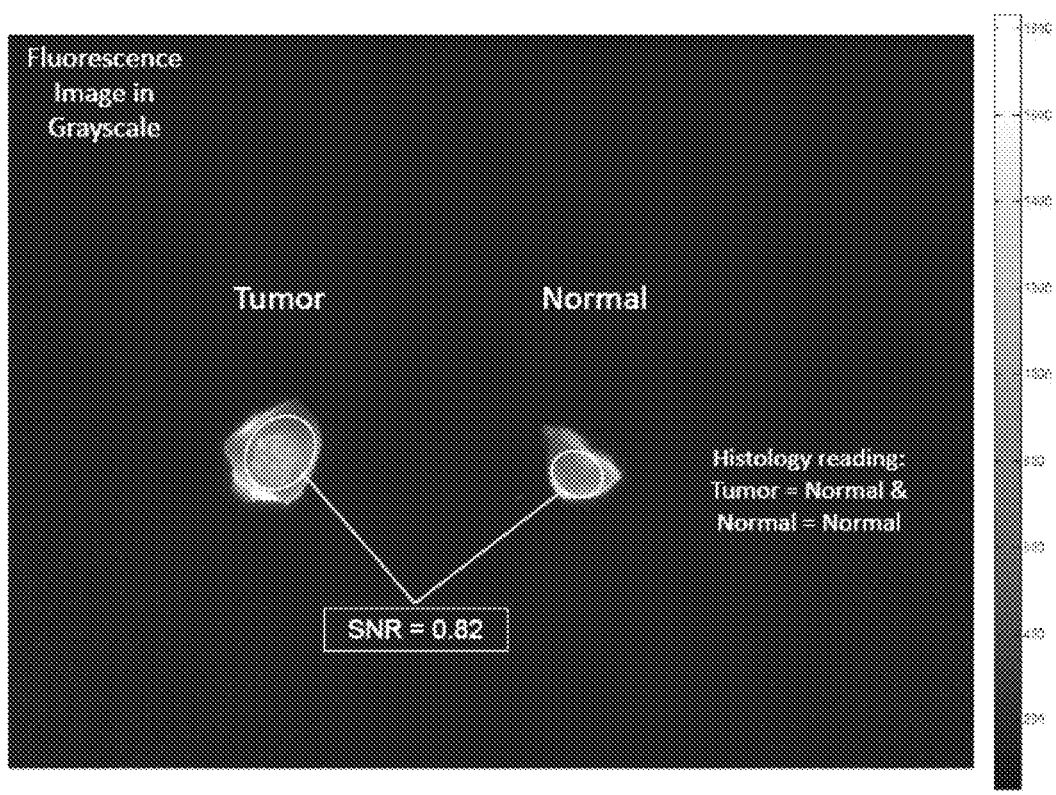
FIG. 26 is a fluorescence image of two tissue samples obtained from patient number 8 and stained with a WGA-fluorophore probe.

Both normal and "suspicious" (from a suspicious looking lesion) tissue samples were obtained by biopsy from the check mucosa of patient 8. The tissue samples were stained with 0.5 ml of 5 µM WGA probe in 10% DMSO solution and incubated for one hour at 37 degrees C. The tissue samples were then washed three times in succession, the first time with 40 ml 1×PBS in 10% DMSO, and the second and third times with 40 ml 1×PBS. The tissue samples were then exposed to an excitation light source, and the resulting fluorescence image is shown in FIG. 26.

The fluorescence intensity scale (in au) is shown to the right of the fluorescence image. In the fluorescence image itself, the "suspicious" tissue sample is on the left and the normal tissue sample is on the right. Histology was used to determine that both tissues were in fact normal. This finding was consistent with the imaging results, where the differential signal ratio between the two samples was calculated to be 0.82, showing only a small difference in fluorescence intensity between the two samples. This result typifies a perfect negative control, since the biopsied lesion was quite indicative of a papilloma which is commonly caused by the human papilloma virus and can further lead to oral cancer; however, the fluorescent staining proved that the tissue was benign, demonstrating the sensitivity and specificity of the approach.

Figure 27:
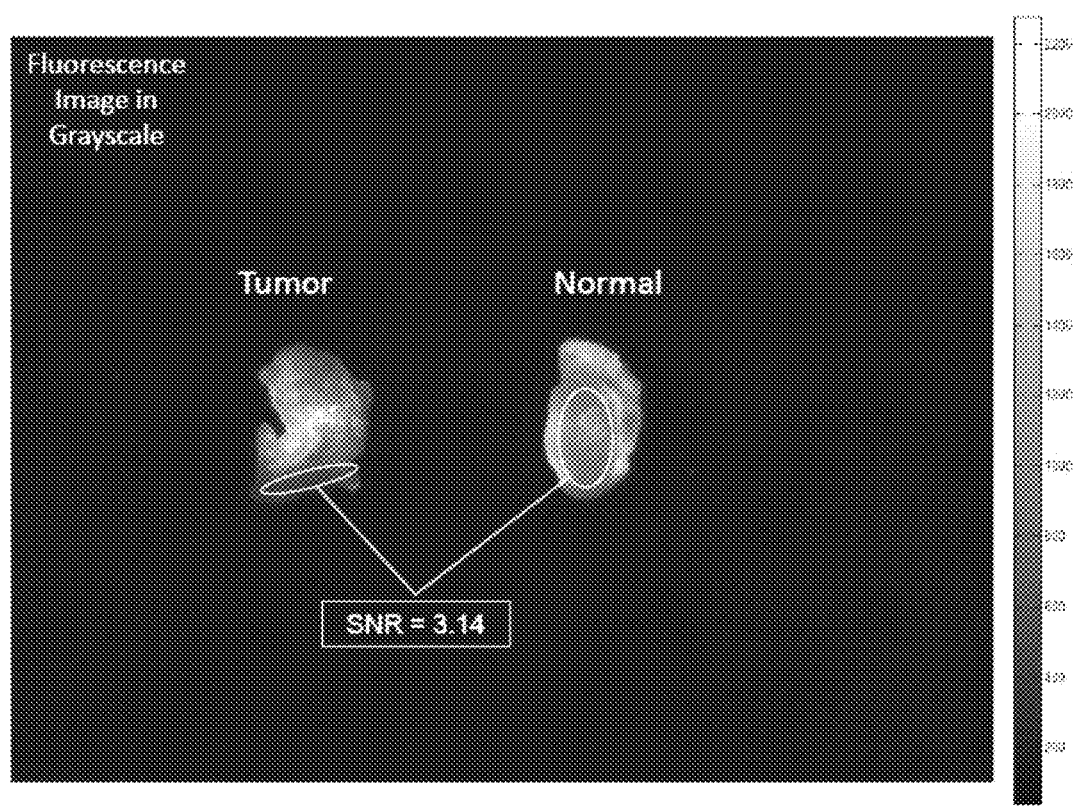
FIG. 27 is a fluorescence image of two tissue samples obtained from patient number 10 and stained with a WGA-fluorophore probe.

Normal and tumor tissue samples were obtained by biopsy from the buccal mucosa of patient 10. The tissue samples were stained with 0.5 ml of 5 µM WGA probe in 10% DMSO solution and incubated for one hour at 37 degrees C. The tissue samples were then washed three times in succession, the first time with 40 ml 1×PBS in 10% DMSO, and the second and third times with 40 ml 1×PBS. The tissue samples were then exposed to an excitation light source, and the resulting fluorescence image is shown in FIG. 27.

The fluorescence intensity scale (in au) is shown to the right of the fluorescence image. In the fluorescence image itself, the normal tissue sample is on the right, and the cancerous tissue is on the left. Based on a comparison of the fluorescence intensity measured from the cancerous tissue (within the leftmost oval) and the normal tissue (within the rightmost oval), the differential signal ratio for this sample was calculated to be 3.14.

Figure 28:
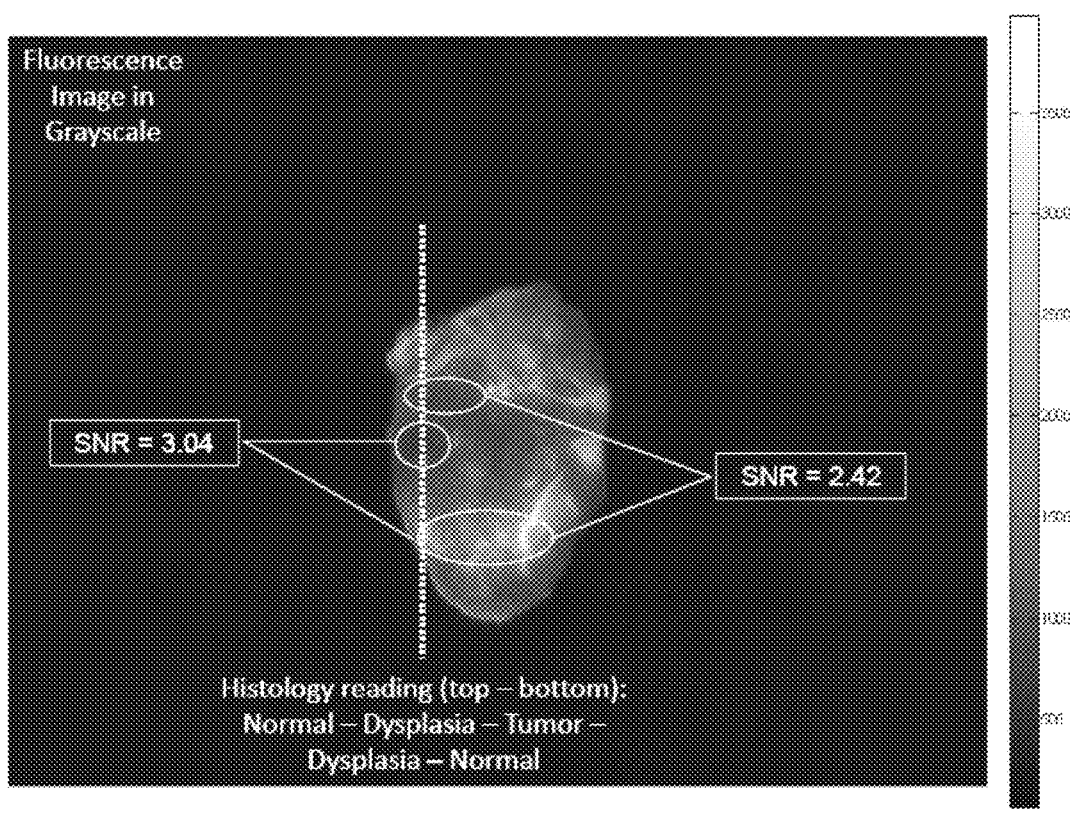
FIG. 28 is a fluorescence image of tissue obtained from patient number 11 and stained with a WGA-fluorophore probe.

Biopsy tissue was obtained from the tongue of patient 11. The tissue was stained with 2 ml of 5 µM WGA probe in 10% DMSO solution and incubated for one hour at 37 degrees C. The tissue was then washed three times in succession, the first time with 40 ml 1×PBS in 10% DMSO, and the second and third times with 40 ml 1×PBS. The tissue was then exposed to an excitation light source, and the resulting fluorescence image is shown in FIG. 28.

The fluorescence intensity scale (in au) is shown to the right of the fluorescence image. Histology done on a frozen section of the tissue along the vertical dotted line revealed tissue change along the line from top to bottom from normal tissue (top of dotted line on sample image) to dysplastic tissue (within the top oval) to cancerous tissue (within the central circle) to dysplastic tissue and back to normal tissue (within the bottom oval). Based on a comparison of the fluorescence intensity measured from the cancerous tissue (within the center circle) and the normal tissue (within the bottom oval), the differential signal ratio was calculated to be 3.04. Based on a comparison of the fluorescence intensity measured from the dysplastic tissue (within the top oval) and the normal tissue (within the bottom oval), the differential signal ratio was calculated to be 2.42.

Fluorescence Imaging Using GS-II Lectin Fluorophore Conjugate.

Figure 29:
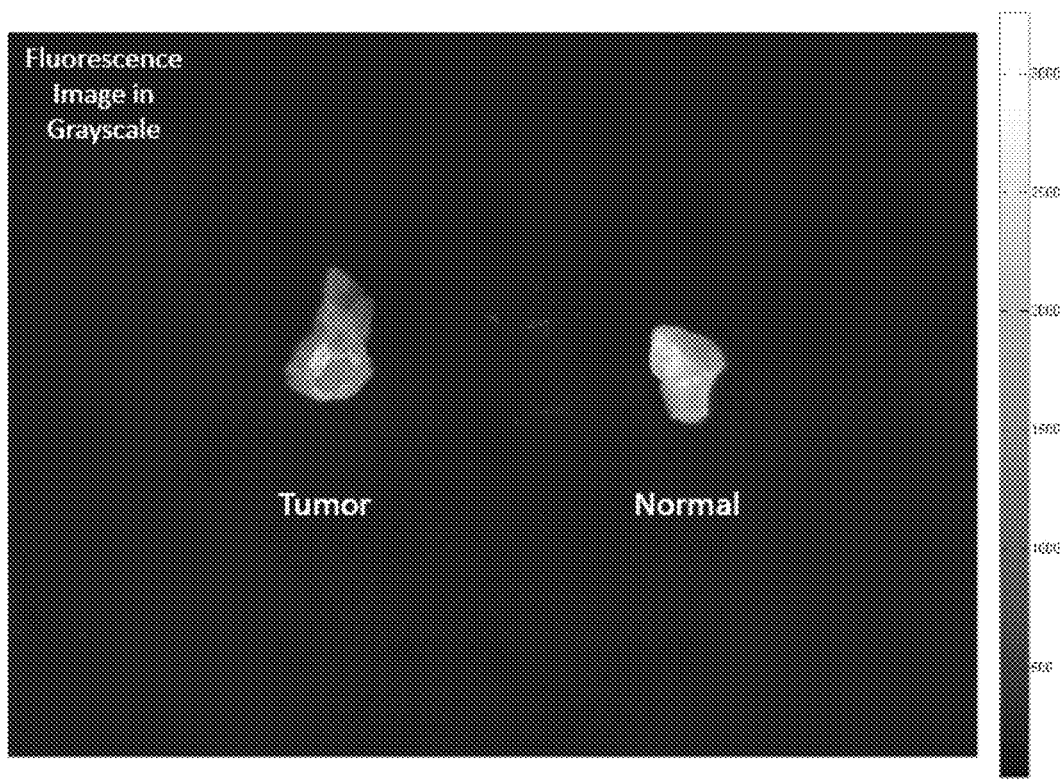
FIG. 29 is a fluorescence image of two tissue samples obtained from patient number 4 and stained with a GS-I-fluorophore probe.

A partial glossectomy was performed on patient 4. Both normal and tumor tissue were removed from the sample obtained by partial glossectomy, and the tissue samples were stained with 0.5 ml of 5 µM GS-II probe in 10% DMSO solution and incubated for one hour at 37 degrees C. The tissue samples were then washed three times in succession, the first time with 40 ml 1×PBS in 10% DMSO, and the second and third times with 40 ml 1×PBS. The tissue samples were then exposed to an excitation light source, and the resulting fluorescence image is shown in FIG. 29.

The fluorescence intensity scale (in au) is shown to the right of the fluorescence image. In the fluorescence image itself, the normal tissue is on the right and the cancerous tissue is shown on the left. As shown in the image, fluorescence intensity was higher in the normal tissue than in the cancerous tissue. Based on a comparison of the fluorescence intensity measured from the cancerous tissue and the normal tissue, the differential signal ratio for this sample was calculated to be 1.43.

Fluorescence Imaging Using PNA Lectin Fluorophore Conjugate.

Figure 30:
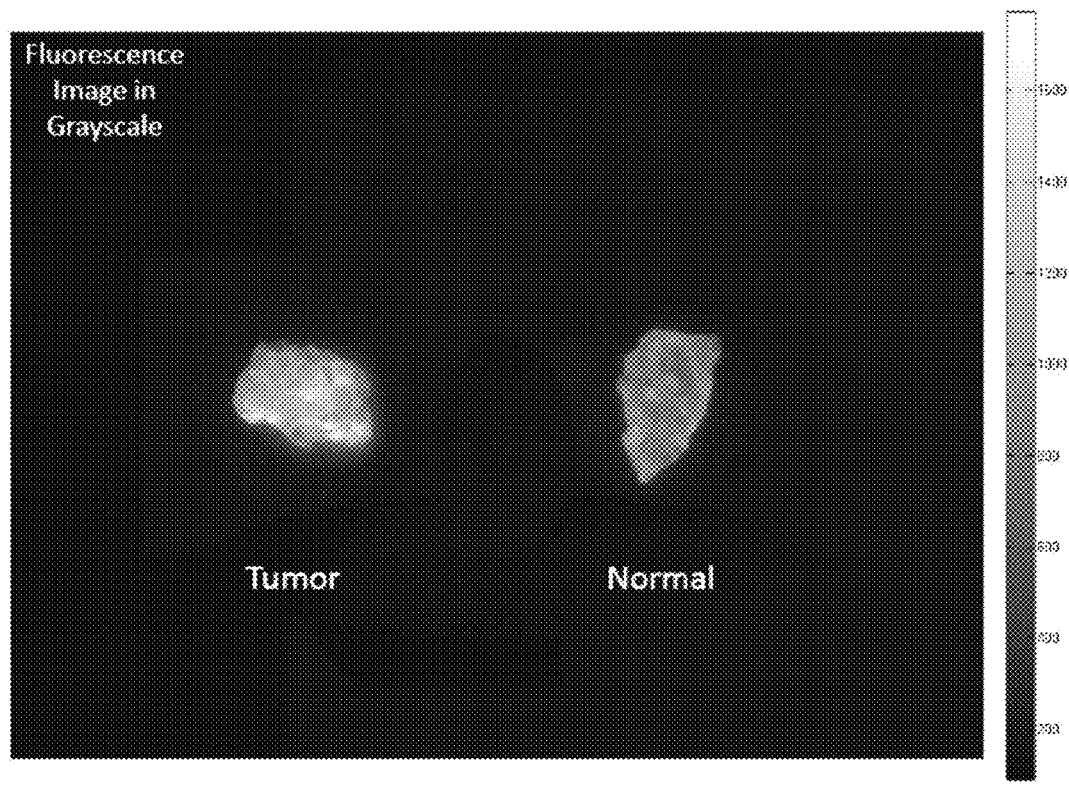
FIG. 30 is a fluorescence image of two tissue samples obtained from patient number 1 and stained with a PNA-fluorophore probe.

Both cancerous and normal biopsy tissue samples were obtained from the base of the tongue of patient 1. The tissue samples were stained with 0.5 ml of 5 µM PNA probe in 10% DMSO solution and incubated for thirty minutes at room temperature. The tissue was then washed three times in succession with 30 ml 1×PBS. The tissue samples were then exposed to an excitation light source, and the resulting fluorescence image is shown in FIG. 30.

The fluorescence intensity scale (in au) is shown to the right of the fluorescence image. In the fluorescence image itself, the normal tissue is on the right and the cancerous tissue is shown on the left. As shown in the image, fluorescence intensity was higher in the cancerous tissue than in the normal tissue. Based on a comparison of the fluorescence intensity measured from the cancerous tissue and the normal tissue, the differential signal ratio for this sample was calculated to be 1.58.

Figure 31:
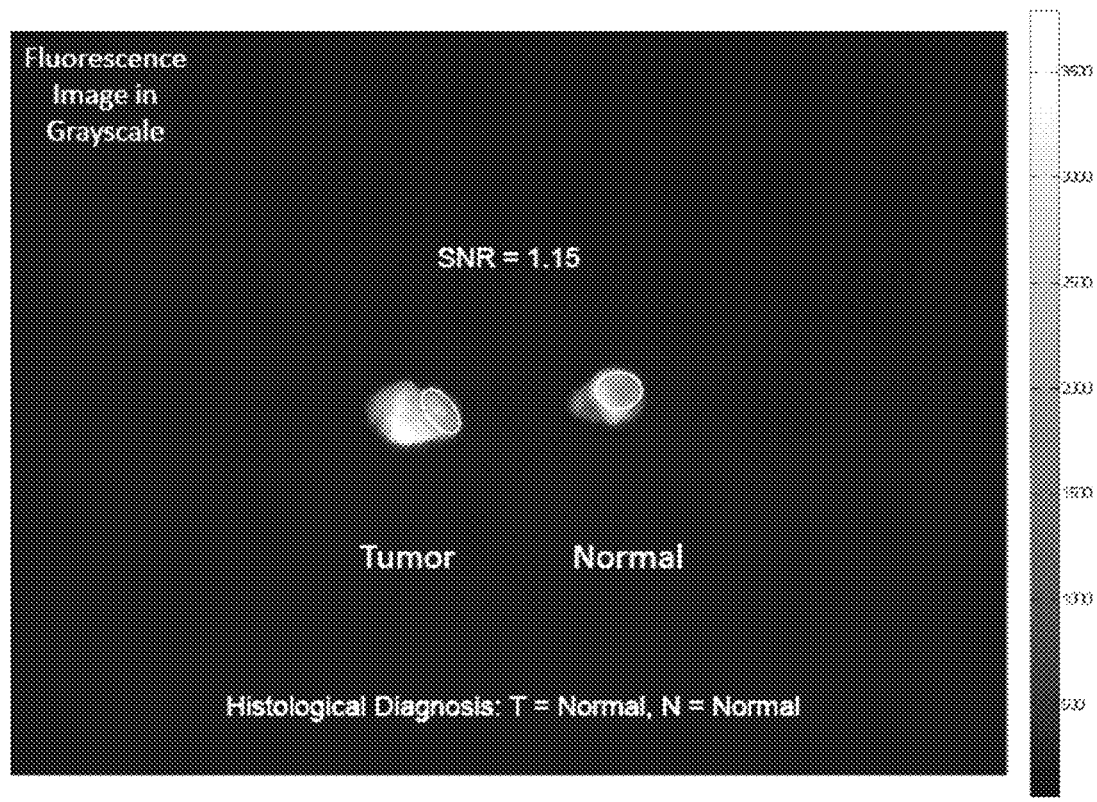
FIG. 31 is a fluorescence image of two tissue samples obtained from patient number 3 and stained with a PNA-fluorophore probe.

Both normal and tumor tissue samples were obtained by biopsy from the buccal mucosa of patient 3. The tissue samples were stained with 0.5 ml of 5 µM PNA probe in 10% DMSO solution and incubated for one hour at 37 degrees C. The tissue samples were then washed three times in succession, the first time with 40 ml 1×PBS in 10% DMSO, and the second and third times with 40 ml 1×PBS. The tissue samples were then exposed to an excitation light source, and the resulting fluorescence image is shown in FIG. 31.

The fluorescence intensity scale (in au) is shown to the right of the fluorescence image. In the fluorescence image itself, the normal tissue sample is on the right and the cancerous tissue sample is shown on the left. Fluorescence intensity was somewhat higher in the normal tissue than in the cancerous tissue. Based on a comparison of the fluorescence intensity measured from the cancerous tissue (within the leftmost oval) and the normal tissue (within the rightmost circle), the differential signal ratio for this sample was calculated to be 1.15.

Discussion

The results demonstrate that autofluorescence using UV excitation wavelengths can provide a quick and reliable means to assess oral health, with a mean differential signal ratio for normal versus cancerous tissue 1.51. Autofluorescence cannot, however, differentiate between precancerous conditions with a clinically significant differential signal ratio, and a higher differential signal ratio would lead to yet more reliable and efficient detection of oral cancer.

Our data demonstrate that the use of WGA fluorophore probes are a significant improvement over autofluorescence methods, providing a consistent and reproducible differential signal ratio for reliably distinguishing normal from cancerous tissue in the oral mucosa. This can be seen clearly in FIG. 31A, which compares the differential signal ratios for the autofluorescence and WGA fluorescent probes in seven of the patients. In all seven patients for which the data is compared, the differential signal ratio is greater using the WGA fluorophore probe than it is for using autofluorescence, and in six of the seven it is at least double the ratio obtained using autofluorescence.

Figure 32A:
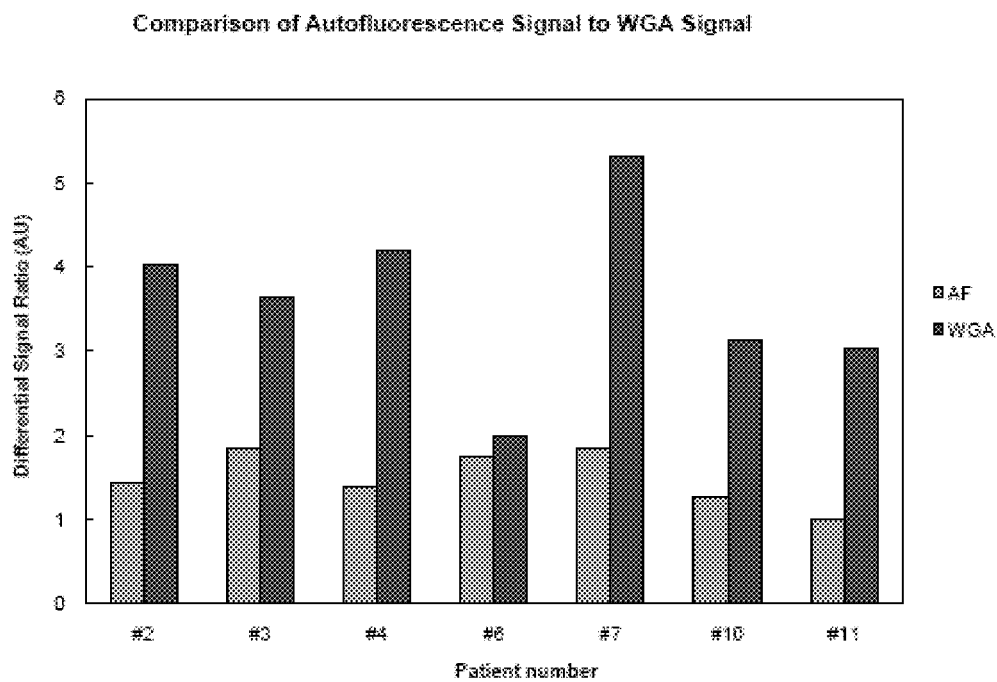
FIG. 32A is a bar graph comparing the differential signal ratio of autofluorescence and WGA fluorescence for tissues from seven different patients.
Figure 32B:
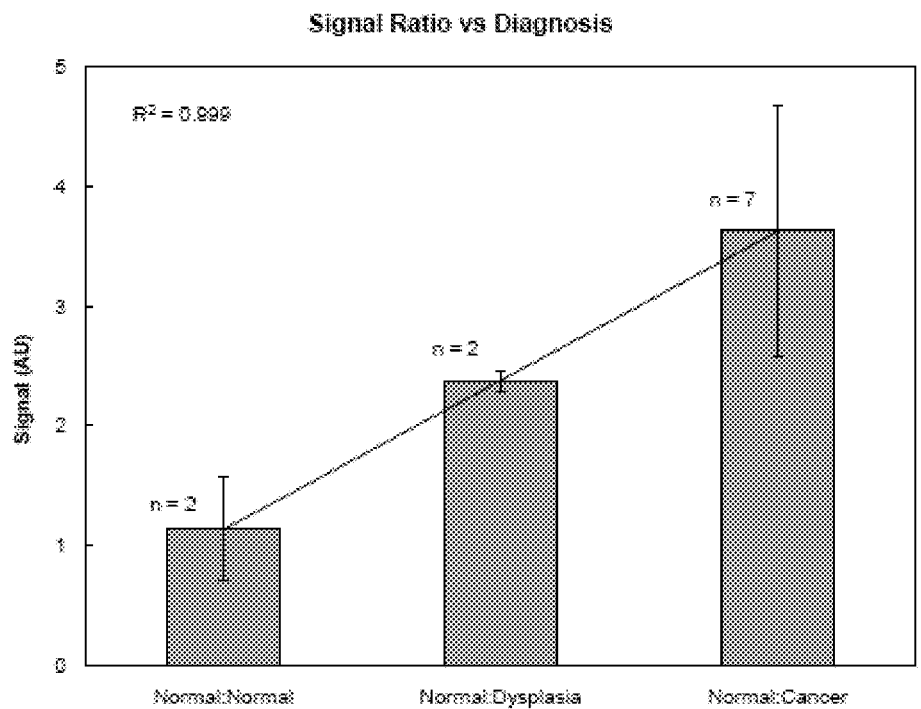
FIG. 32B is a bar graph showing average differential signal ratio using WGA fluorescence as a function of tissue types being compared.

In addition, when using WGA fluorophore probes, signal levels for dysplastic tissue and other early cancers is significantly different than for normal tissue, indicating that the method could be used successfully not only to detect cancer, but to detect dysplasia and other pre-cancers. This is shown in FIG. 32B, which illustrates the clear differential in differential signal ratio when comparing normal to cancerous tissue (rightmost bar), normal to dysplastic tissue (center bar), and normal to normal tissue (leftmost bar). The three comparison groups exhibited significantly different differential signal ratios, with p<0.05. Because the signal intensity emitted by the WGA fluorophore probes varies linearly with disease progression, the method may be broadly applicable to detecting surgical margins and providing additional prognostic and diagnostic data.

Our data obtained using GS-II fluorescent probes further suggest that other lectins can and do bind to the same moieties targeted by WGA. Like the WGA probe, the GS-II probe exhibited increased signal intensity in normal tissue as compared to cancerous tissue, demonstrating that probe specificity can be generalized to other lectin probes.

Our data obtained using PNA fluorescent probes demonstrates another target for lectin-based differentiation between neoplastic and normal tissues. Unlike the GS-II and WGA probes, the PNA probe exhibited increased signal intensity in cancerous tissue as compared to normal tissue, suggesting that a variety of targets can facilitate cancer detection using lectin based probes.

CONCLUSION

To the best of their knowledge, the inventors have for the first time demonstrated herein that topical application of lectin probes to mucosal epithelial tissues followed by molecular imaging of the tissues can be used to spatially resolve cancerous, precancerous, and normal tissue with a high differential signal ratio.

The present invention has been described in connection with what are considered to be the most practical and preferred embodiments. However, the invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method of in vivo imaging an oral mucosal surface of a subject to assess aberrant glycosylation patterns; the method comprising the steps of:
   (a) topically applying one or more lectin-fluorophore conjugates consisting of a lectin covalently bonded to a fluorescent label directly to the oral mucosal surface of the subject in vivo, wherein the lectin is selected from the group consisting of wheat germ agglutinin lectin (WGA), peanut agglutinin lectin (PNA), and griffonia *simplicifolia* lectin (GS-II);
   (b) exciting the one or more lectin-fluorophore conjugates in vivo; and
   (c) observing the emitted fluorescent signal in vivo, wherein an observable fluorescence difference between adjacent regions is indicative of aberrant glycosylation; wherein the fluorescence difference is observed without extracting tissue from the subject.

2. The method of claim 1, further comprising the step of directly applying in vivo to at least a portion of the oral mucosal surface a pretreatment solution that facilitates lectin binding, wherein the step of directly applying the pretreatment solution is performed prior to topically applying the one or more lectin-fluorophore conjugates to the oral mucosal surface.

3. The method of claim 1, wherein the step of topically applying the one or more lectin-fluorophore conjugates directly to the oral mucosal surface of the subject in vivo is performed by one or more of:
   using a cotton swab, applying a solution comprising the one or more lectin-fluorophore conjugates as an oral rinse, applying a solution comprising the one or more lectin-fluorophore conjugates as a lotion, injecting a solution comprising the one or more lectin-fluorophore conjugates onto the oral mucosal surface, mechanically agitating a solution comprising the one or more lectin-fluorophore conjugates, or ultrasonically agitating a solution comprising the one or more lectin-fluorophore conjugates.

4. The method of claim 1, wherein the one or more lectin-fluorophore conjugates are topically applied using a solution having a lectin concentration of 1-10 micromolar.

5. The method of claim 1, wherein the one or more lectin-fluorophore conjugates are topically applied using a solution that further comprises a buffering agent.

6. The method of claim 1, wherein the one or more lectin-fluorophore conjugates are topically applied using a solution that further comprises one or more permeation enhancers.

7. The method of claim 1 wherein the step of exciting the one or more lectin-fluorophore conjugates comprises one or more of:
   waiting to perform the observing step to allow time for the lectin-fluorophore conjugates to penetrate the oral mucosal surface, rinsing the oral mucosal surface with a solution to clear any unbound lectin-fluorophore conjugate present, serially rinsing the oral mucosal surface to clear any unbound lectin-fluorophore conjugate present, mechanically agitating the oral mucosal surface to clear any unbound lectin-fluorophore conjugate present, ultrasonically agitating the oral mucosal surface to clear any unbound lectin-fluorophore conjugate present, swabbing or rubbing the oral mucosal surface to clear any unbound lectin-fluorophore conjugate present, or illuminating the oral mucosal surface with visible, ultraviolet, or near infrared light.

8. The method of claim 1, wherein the step of observing the emitted fluorescent signal comprises one or more of;
   visualizing the oral mucosal surface by the naked eye, visualizing the oral mucosal surface through a handheld filter or filter glasses, using a camera, using an image processing device and software, or using an optical element or elements selected from a dichroic mirror, a neutral density filter, a polarizer, a microscope, or a combination thereof.

9. The method of claim 1, further comprising one or more additional steps for further processing the emitted fluorescent signal selected from the group consisting of taking optical measurements, normalizing any optical measurements taken, comparing the results obtained in the observing step to a patient bank of normal values, determining the subject's normal fluorescence in a region of interest, and using mathematical processing software to further analyze the results obtained in the observing step.

10. A method of in vivo imaging an oral mucosal surface of a subject to assess aberrant glycosylation patterns; the method comprising the steps of:
    (a) topically applying one or more lectin-fluorophore conjugates consisting of a lectin covalently bonded to a fluorescent label directly to the oral mucosal surface of the subject in vivo, wherein the lectin is selected from the group consisting of wheat germ agglutinin lectin (WGA), peanut agglutinin lectin (PNA), and griffonia *simplicifolia* lectin (GS-II);

(b) exciting the one or more lectin-fluorophore conjugates in vivo, whereby the one or more lectin-fluorophore conjugates emits a fluorescent signal; and (c) observing the emitted fluorescent signal exhibited by the oral mucosal surface of the subject in vivo, wherein an observable fluorescent intensity difference between adjacent regions of the oral mucosal surface indicates aberrant glycosylation patterns on the oral mucosal surface;

wherein the fluorescent intensity difference is observed without extracting tissue from the subject.

11. The method of claim 10, further comprising the step of directly applying in vivo to at least a portion of the oral mucosal surface a pretreatment solution that facilitates lectin binding, wherein the step of directly applying the pretreatment solution is performed prior to topically applying the one or more lectin-fluorophore conjugates to the oral mucosal surface.

12. The method of claim 10, wherein the step of topically applying the one or more lectin-fluorophore conjugates directly to the oral mucosal surface of the subject in vivo is performed by one or more of:

using a cotton swab, applying a solution comprising the one or more lectin-fluorophore conjugates as an oral rinse, applying a solution comprising the one or more lectin-fluorophore conjugates as a lotion, injecting a solution comprising the one or more lectin-fluorophore conjugates lectins onto the oral mucosal surface, mechanically agitating a solution comprising the one or more lectin-fluorophore conjugates, or ultrasonically agitating a solution comprising the one or more lectin-fluorophore conjugates.

13. The method of claim 10 wherein the step of exciting the one or more lectin-fluorophore conjugates comprises one or more of:

waiting to perform the observing step to allow time for the lectin-fluorophore conjugates to penetrate the oral mucosal surface, rinsing the oral mucosal surface with a solution to clear any unbound lectin-fluorophore conjugate present, serially rinsing the oral mucosal surface to clear any unbound lectin-fluorophore conjugate present, mechanically agitating the oral mucosal surface to clear any unbound lectin-fluorophore conjugate present, ultrasonically agitating the oral mucosal surface to clear any unbound lectin-fluorophore conjugate present, swabbing or rubbing the oral mucosal surface to clear any unbound lectin-fluorophore conjugate present, or illuminating the oral mucosal surface with visible, ultraviolet, or near infrared light.

14. The method of claim 10, wherein the step of observing the emitted fluorescent signal comprises one or more of;

visualizing the oral mucosal surface by the naked eye, visualizing the oral mucosal surface through a handheld filter or filter glasses, using a camera, using an image processing device and software, or using an optical element or elements selected from a dichroic mirror, a neutral density filter, a polarizer, a microscope, or a combination thereof.

* * * * *